US012286122B2

United States Patent
Watanabe

(10) Patent No.: US 12,286,122 B2
(45) Date of Patent: Apr. 29, 2025

(54) OPERATION APPROPRIATENESS DETERMINATION SYSTEM, METHOD FOR DETERMINING OPERATION APPROPRIATENESS, AND NON-TRANSITORY COMPUTER READABLE MEDIUM STORING PROGRAM FOR DETERMINING OPERATION APPROPRIATENESS

(71) Applicant: Panasonic Intellectual Property Management Co., Ltd., Osaka (JP)

(72) Inventor: Hisashi Watanabe, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 272 days.

(21) Appl. No.: 17/848,082

(22) Filed: Jun. 23, 2022

(65) Prior Publication Data
US 2022/0315010 A1 Oct. 6, 2022

Related U.S. Application Data

(63) Continuation of application No. 16/414,363, filed on May 16, 2019, now Pat. No. 11,407,422, which is a (Continued)

(30) Foreign Application Priority Data

Feb. 28, 2017 (JP) .................. 2017-035796
Feb. 2, 2018 (JP) .................. 2018-016972

(51) Int. Cl.
*B60W 40/08* (2012.01)
*B60W 50/14* (2020.01)
(Continued)

(52) U.S. Cl.
CPC ............ *B60W 40/08* (2013.01); *B60W 50/14* (2013.01); *G06F 21/32* (2013.01); *H04N 5/33* (2013.01);
(Continued)

(58) Field of Classification Search
CPC ................ B60W 40/08; B60W 50/14; B60W 2540/043; B60W 2040/0809; B60W 2420/403; G06F 21/32; H04N 5/33
See application file for complete search history.

(56) References Cited

U.S. PATENT DOCUMENTS 9,988,055 B1 * 6/2018 O'Flaherty ............ G08B 21/06
2003/0061187 A1 3/2003 Fukui et al.
(Continued)

FOREIGN PATENT DOCUMENTS

JP 5-054300 3/1993
JP 8-225028 9/1996
(Continued)

OTHER PUBLICATIONS

Notice of Allowance dated Mar. 25, 2022 issued in U.S. Appl. No. 16/414,363.
(Continued)

*Primary Examiner* — Dale W Hilgendorf
*Assistant Examiner* — Hana Lee
(74) *Attorney, Agent, or Firm* — Rimon P.C.

(57) ABSTRACT

An operation appropriateness determination system includes an authentication apparatus that identifies an operator on a basis of a feature of the operator and that outputs information for identifying the operator, a biometric sensing apparatus that obtains biological information regarding the operator and that outputs the biological information, an operation sensing apparatus that detects a load of an operation that is being performed by the operator and that outputs
(Continued)

operation information indicating the load of the operation, a storage device, and a signal processing apparatus.

8 Claims, 14 Drawing Sheets

Related U.S. Application Data continuation of application No. PCT/JP2018/004777, filed on Feb. 13, 2018.

(51) Int. Cl.
*G06F 21/32* (2013.01)
*H04N 5/33* (2023.01)

(52) U.S. Cl.
CPC ............ *B60W 2040/0809* (2013.01); *B60W 2420/403* (2013.01); *B60W 2540/043* (2020.02)

(56) References Cited

U.S. PATENT DOCUMENTS

| | | | |
|---|---|---|---|
| 2006/0094938 A1 | 5/2006 | Shimada et al. | |
| 2009/0244288 A1 | 10/2009 | Fujimoto et al. | |
| 2013/0131521 A1 | 5/2013 | Yoshioka et al. | |
| 2013/0160111 A1 | 6/2013 | Orr | |
| 2015/0164400 A1 | 6/2015 | Shimizu et al. | |
| 2015/0186612 A1* | 7/2015 | Gartseev | H04W 4/50 702/19 |
| 2015/0317465 A1 | 11/2015 | McCarty et al. | |
| 2016/0063883 A1 | 3/2016 | Jeyanandarajan | |
| 2016/0151021 A1* | 6/2016 | Feng | A61B 5/7282 600/484 |
| 2016/0283703 A1 | 9/2016 | Allyn | |
| 2016/0291592 A1* | 10/2016 | Matthews | G06T 3/16 |
| 2016/0332567 A1* | 11/2016 | Wilson | G01S 19/14 |
| 2016/0345907 A1 | 12/2016 | Fung et al. | |
| 2016/0354027 A1 | 12/2016 | Benson et al. | |
| 2017/0035332 A1 | 2/2017 | Wahnschafft | |
| 2017/0194370 A1 | 7/2017 | Mase et al. | |
| 2018/0009442 A1* | 1/2018 | Spasojevic | A61B 5/0205 |
| 2018/0046790 A1 | 2/2018 | Jones et al. | |

FOREIGN PATENT DOCUMENTS

| | | |
|---|---|---|
| JP | 10-315800 | 12/1998 |
| JP | 11-203006 A | 7/1999 |
| JP | 2002-065650 | 3/2002 |
| JP | 2003-098947 | 4/2003 |
| JP | 2004-089272 | 3/2004 |
| JP | 2006-129887 | 5/2006 |
| JP | 2007-099249 | 4/2007 |
| JP | 2007-159762 | 6/2007 |
| JP | 2009-037415 A | 2/2009 |
| JP | 2009-146192 | 7/2009 |
| JP | 2009-226057 | 10/2009 |
| JP | 2009-226057 A | 10/2009 |
| JP | 2009-246903 | 10/2009 |
| JP | 2011-039767 A | 2/2011 |
| JP | 2014-202733 | 10/2014 |
| JP | 2016-018314 A | 2/2016 |
| WO | 2012/150657 | 11/2012 |

OTHER PUBLICATIONS

International Search Report of PCT application No. PCT/JP2018/004777 dated May 1, 2018.
The Extended European Search Report dated Feb. 3, 2020 for the related European Patent Application No. 18761519.0.
O' Sullivan et al., Diffuse Optical Imaging Using Spatially and Temporally Modulated Light, Jul. 18, 2012, Journal of Biomedical Optics (Year: 2012).
Non-Final Office Action dated Mar. 16, 2021 issued in U.S. Appl. No. 16/414,363.
Final Office Action dated Sep. 13, 2021 issued in U.S. Appl. No. 16/414,363.

* cited by examiner

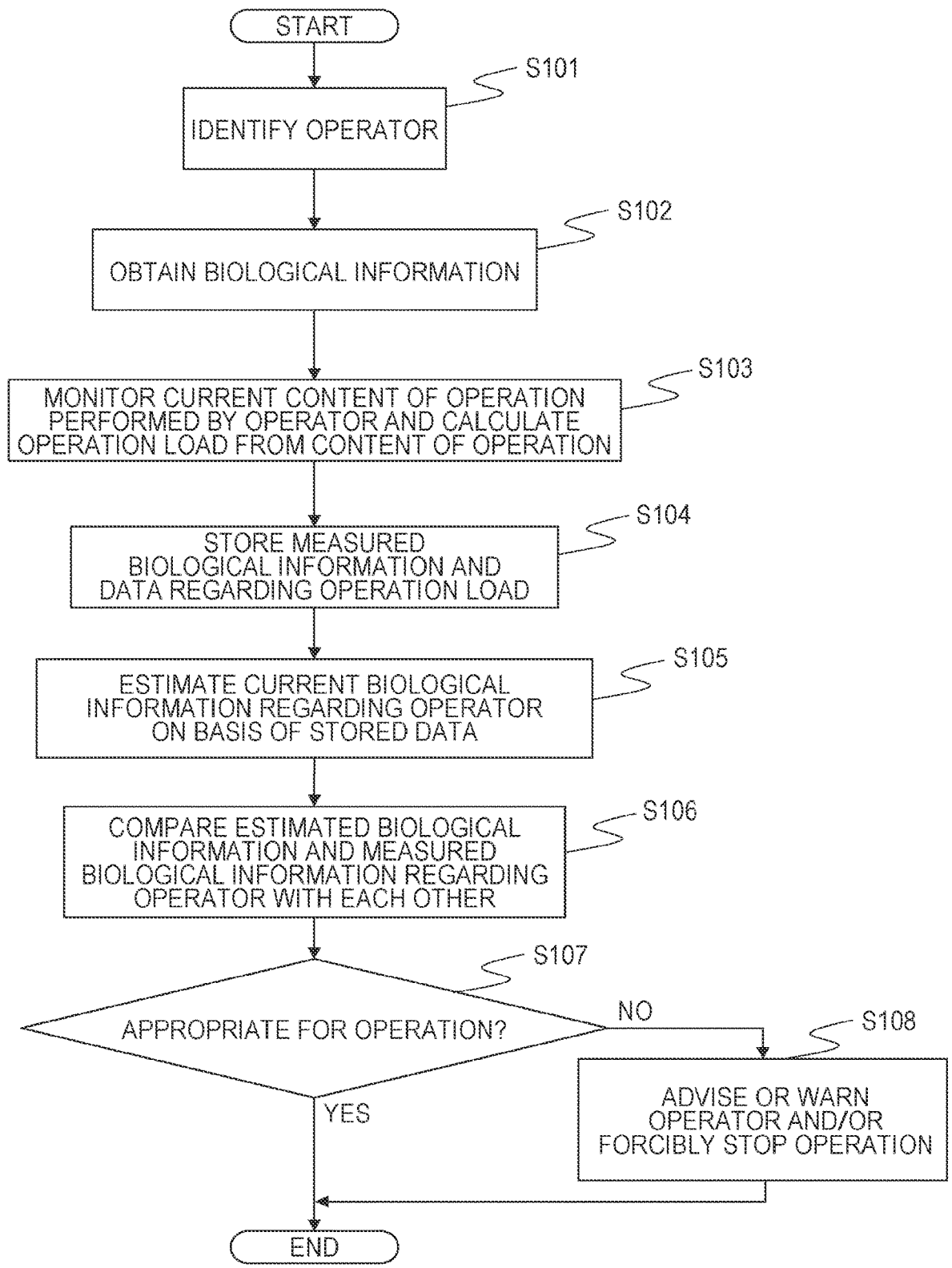

OPERATION APPROPRIATENESS DETERMINATION SYSTEM, METHOD FOR DETERMINING OPERATION APPROPRIATENESS, AND NON-TRANSITORY COMPUTER READABLE MEDIUM STORING PROGRAM FOR DETERMINING OPERATION APPROPRIATENESS

CROSS-REFERENCE TO RELATED APPLICATIONS

This application is a continuation of U.S. patent application Ser. No. 16/414,363, filed May 16, 2019, which is a continuation of International Patent Application No. PCT/JP2018/004777, filed Feb. 13, 2018, which claims priority to Japanese Patent Application No. 2017-035796, filed on Feb. 28, 2017; and Japanese Patent Application No. 2018-016972, filed on Feb. 2, 2018, the entire disclosures each of which are hereby incorporated by reference.

BACKGROUND

1. Technical Field

The present invention relates to a system that determines current operation appropriateness of an operator, a method, and a non-transitory computer readable medium storing a program.

2. Description of the Related Art

Mental concentration is extremely important in daily operations. If a person performs an operation without attention, efficiency decreases, and an accident can be caused. If a person loses concentration during an operation, for example, operation efficiency decreases, and productivity also decreases. Lack of concentration or sleepiness during driving of a vehicle can directly lead to a traffic accident. If concentration can be constantly monitored and an appropriate advice or assistance can be provided in accordance with a degree of concentration or nervousness at the time, operation efficiency or safety can improve. A large number of such measures have actually been proposed. A technique for determining a degree of mental concentration from various types of biological information and providing an advice or assistance in accordance with the degree of concentration, for example, has been proposed. Japanese Unexamined Patent Application Publication No. 2002-65650, Japanese Patent No. 6003782, and Japanese Patent No. 5119375 have disclosed examples of such a technique.

SUMMARY

In one general aspect, the techniques disclosed here feature an operation appropriateness determination system including an authentication apparatus that identifies an operator on a basis of a feature of the operator and that outputs information for identifying the operator, a biometric sensing apparatus that obtains biological information regarding the operator and that outputs the biological information, an operation sensing apparatus that detects a load of an operation that is being performed by the operator and that outputs operation information indicating the load of the operation, a storage device, and a signal processing apparatus. The signal processing apparatus accumulates, while the operator is performing the operation, the information for identifying the operator, the biological information, the operation information, and time information in the storage device while associating the information for identifying the operator, the biological information, the operation information, and the time information with one another, estimates the biological information regarding the operator at a present time on a basis of a correlation between temporal changes in the operation information and temporal changes in the biological information in past accumulated in the storage device, and determines appropriateness of the operator for the operation by comparing the estimated biological information regarding the operator at the present time and the biological information regarding the operator at the present time obtained by the biometric sensing apparatus with each other.

It should be noted that general or specific aspects of the present disclosure may be implemented by a device, an apparatus, a system, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1B is a diagram illustrating an example of the operation of the operation appropriateness determination system according to the exemplary embodiment of the present disclosure;

DETAILED DESCRIPTION

Figure 1A:
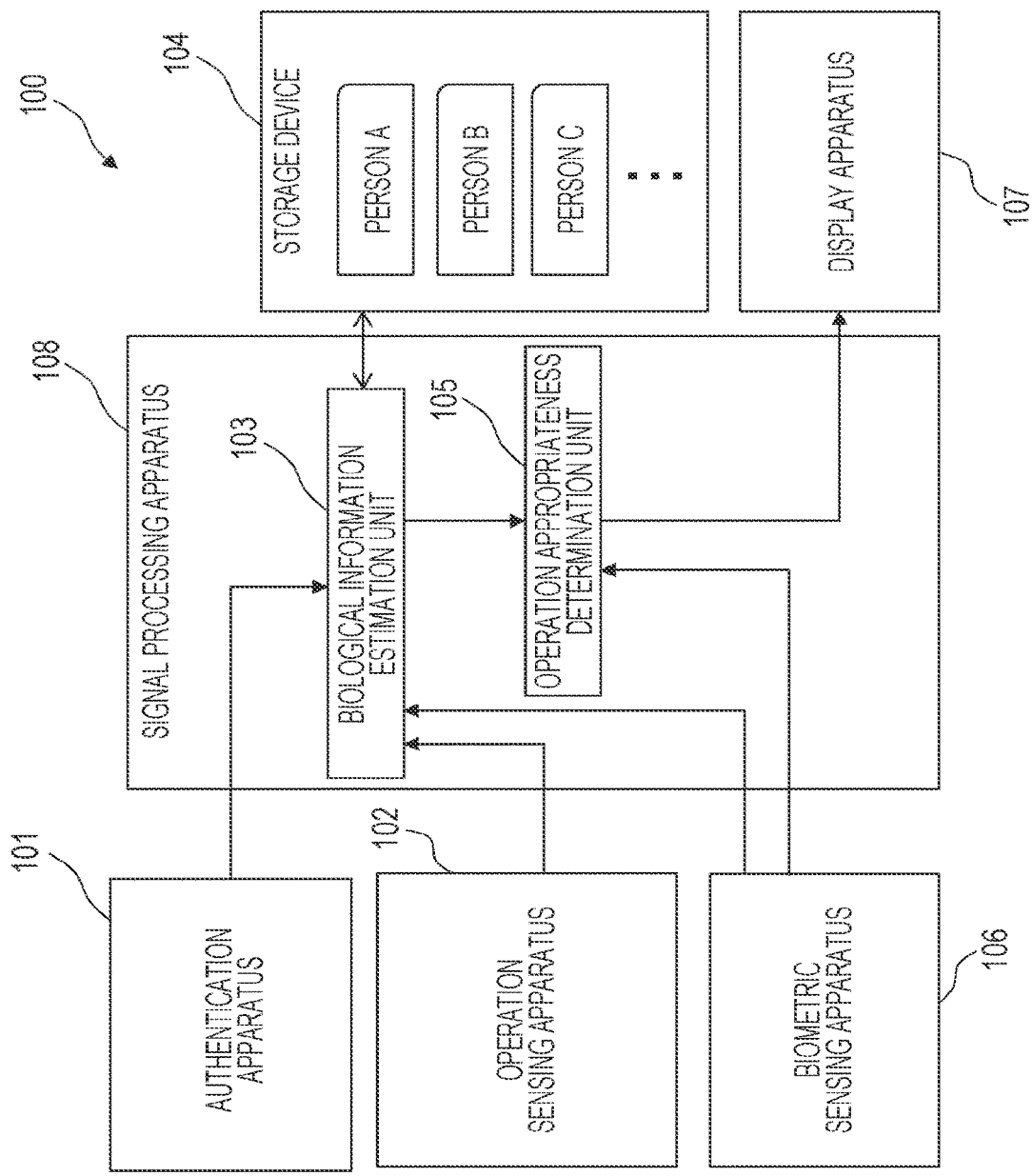
FIG. 1A is a diagram illustrating the configuration of an operation appropriateness determination system according to an exemplary embodiment of the present disclosure.

The present disclosure includes an operation appropriateness determination system, a method, and a computer program described in the following items.

Item 1

An operation appropriateness determination system according to Item 1 of the present disclosure includes:

an authentication apparatus that identifies an operator on a basis of a feature of the operator and that outputs information for identifying the operator;

a biometric sensing apparatus that obtains biological information regarding the operator and that outputs the biological information;

an operation sensing apparatus that detects a load of an operation that is being performed by the operator and that outputs operation information indicating the load of the operation;

a storage device; and a signal processing apparatus.

The signal processing apparatus accumulates, while the operator is performing the operation, the information for identifying the operator, the biological information, the operation information, and time information in the storage device while associating the information for identifying the operator, the biological information, the operation information, and the time information with one another, estimates the biological information regarding the operator at a present time on a basis of a correlation between temporal changes in the operation information and temporal changes in the biological information in past accumulated in the storage device, and determines appropriateness of the operator for the operation by comparing the estimated biological information regarding the operator at the present time and the biological information regarding the operator at the present time obtained by the biometric sensing apparatus with each other.

Item 2

In the operation appropriateness determination system according to Item 1, the authentication apparatus may include an input device that enables the operator to input a person authentication code before performing the operation, and the authentication apparatus may identify the operator on a basis of the person authentication code.

Item 3

In the operation appropriateness determination system according to Item 1, the authentication apparatus may include a biometric authentication device that identifies the operator using at least one selected from the group consisting of a fingerprint, a palm print, an iris, and a vein pattern.

Item 4

The operation appropriateness determination system according to Item 1, may further include:

an imaging device that captures an image of the operator and that obtains data regarding the image.

The authentication apparatus may identify the operator on a basis of the data regarding the image.

Item 5

In the operation appropriateness determination system according to any of Items 1 to 4, the biometric sensing apparatus may be arranged at a point distant from the operator, include an imaging element that captures an image including a head of the operator and that obtains data regarding the image, and obtain the biological information regarding the operator on a basis of the data regarding the image.

Item 6

In the operation appropriateness determination system according to any of Items 1 to 4, the biometric sensing apparatus may include a light source that emits near-infrared light which is spatially or temporally modulated, and an imaging element that captures an image including a face of the operator illuminated by the light source.

Item 7

In the operation appropriateness determination system according to Item 6, the near-infrared light may be spatially modulated using a dot array pattern, a line-space pattern, or a checker pattern.

Item 8

In the operation appropriateness determination system according to Item 6, the near-infrared light may be pulsed light, and the imaging element may include at least one charge accumulator that receives the pulsed light and that accumulates signal charge.

Item 9

In the operation appropriateness determination system according to any of Items 1 to 8, the signal processing apparatus may estimate the biological information regarding the operator at the present time by analyzing the correlation accumulated in the storage device through a multivariate analysis.

Item 10

In the operation appropriateness determination system according to any of Items 1 to 8, the signal processing apparatus may learn the correlation stored in the storage device through machine learning and estimates the biological information regarding the operator at the present time on a basis of a learning result.

Item 11

In the operation appropriateness determination system according to any of Items 1 to 10, the operator may be a driver of a vehicle, the operation may be driving of the vehicle, and the operation information may be information regarding an operation for driving the vehicle.

Item 12

In the operation appropriateness determination system according to Item 11, the operation for driving the vehicle may include at least one operation selected from the group consisting of acceleration, braking, and steering.

Item 13

In the operation appropriateness determination system according to Item 11 or 12, the operation sensing apparatus may include an acceleration sensor, and the signal processing apparatus may estimate information regarding the operation for driving the vehicle on a basis of information output from the acceleration sensor.

Item 14

In the operation appropriateness determination system according to any of Items 11 to 13, the vehicle may have an autonomous driving function including driving assistance, and the signal processing apparatus may determine content of the driving assistance in accordance with the appropriateness of the driver and cause the vehicle to perform the driving assistance.

Item 15

In the operation appropriateness determination system according to any of Items 1 to 10, the operation may be an input operation in which a computer is used, and the operation information may be information regarding an operation input to the computer.

Item 16

In the operation appropriateness determination system according to Item 15, the operation may include at least one operation selected from the group consisting of a keyboard input and a mouse operation.

Item 17

In the operation appropriateness determination system according to Item 15 or 16, the signal processing apparatus may cause the computer to output an image or a sound indicating advice about the input operation in accordance with the appropriateness of the operator.

Item 18

In the operation appropriateness determination system according to any of Items 1 to 10, the operation may be learning in which a computer is used, and the operation information may be information regarding content of the learning and an operation performed using the computer.

Item 19

In the operation appropriateness determination system according to Item 18, the signal processing apparatus may cause the computer to provide learning content according to the appropriateness of the operator.

Item 20

A method for determining appropriateness of an operator for an operation according to Item 20 of the present disclosure includes:

obtaining information for identifying the operator, biological information regarding the operator who is performing the operation, and operation information indicating a load of the operation;

accumulating the information for identifying the operator, the biological information, the operation information, and time information in a storage device while associating the information for identifying the operator, the biological information, the operation information, and the time information with one another;

estimating the biological information regarding the operator at a present time on a basis of a correlation between temporal changes in the operation information and temporal changes in the biological information in past accumulated in the storage device; and determining the appropriateness of the operator for the operation at the present time by comparing the estimated biological information regarding the operator at the present time and the obtained biological information regarding the operator at the present time.

Item 21

A non-transitory computer readable medium according to Item 21 of the present disclosure stores a computer program causing a computer to perform a process including:

obtaining information for identifying an operator, biological information regarding the operator who is performing an operation, and operation information indicating a load of the operation;

accumulating the information for identifying the operator, the biological information, the operation information, and time information in a storage device while associating the information for identifying the operator, the biological information, the operation information, and the time information with one another;

estimating the biological information regarding the operator at a present time on a basis of a correlation between temporal changes in the operation information and temporal changes in the biological information in past accumulated in the storage device; and determining appropriateness of the operator for the operation at the present time by comparing the estimated biological information regarding the operator at the present time and the obtained biological information regarding the operator at the present time.

Embodiments that will be described hereinafter are general or specific examples. Values, shapes, materials, components, positions at which the components are arranged, and the like mentioned in the following embodiments are examples, and do not limit the techniques in the present disclosure. Among the components described in the following embodiments, ones not described in the independent claims, which define broadest concepts, will be described as optional components.

In the present disclosure, some or all of circuits, units, apparatuses, members, or sections or some or all of functional blocks illustrated in the block diagrams, for example, may be achieved by one or a plurality of electronic circuits including a semiconductor device, a semiconductor integrated circuit (IC), or an large-scale integration (LSI) circuit. The LSI circuit or the IC may be integrated on a single chip, or may be obtained by combining a plurality of chips. The functional blocks other than storage devices, for example, may be integrated on a single chip. Although the term "LSI" or "IC" is used here, "system LSI", "very-large-scale integration (VLSI)", or "ultra-large-scale integration (ULSI)" may be used depending on a degree of integration. A field-programmable gate array (FPGA), which is programmed after an LSI circuit is fabricated, or a reconfigurable logic device, in which connections inside an LSI circuit can be reconfigured or circuit sections inside the LSI can be set up, may be used for the same purposes.

Furthermore, functions or operations of some or all of the circuits, the units, the apparatuses, the members, or the sections may be achieved through software processes. In this case, software is stored in one or a plurality of non-transitory storage media, such as read-only memories (ROMs), optical discs, or hard disk drives, and functions specified by the software are achieved by a processor and peripheral apparatuses when the processor has executed the software. A system or an apparatus may include the one or plurality of non-transitory storage media in which the software is stored, the processor, and necessary hardware devices, such as interfaces.

Underlying Knowledge Forming Basis of the Present Disclosure

Underlying knowledge forming a basis of the present disclosure will be described before the embodiments of the present disclosure will be described.

As described above, whether a mental state of a person during an operation is appropriate for the operation is an extremely important factor that influences not only efficiency of the operation but also safety of the operation. Various measures have therefore been taken to estimate mental states. Various types of biological information have been detected in order to estimate mental states such as nervousness, vigilance, and concentration. Biological information such as a heart rate, fluctuation in a heart rate, a respiratory rate, fluctuation in a respiratory rate, the depth of respiration, blood pressure, brain waves, cerebral blood flow (CBF), pupil diameter, nose temperature, blinking, and movement of a line of sight has been used. There are, however, roughly three major problems in methods for directly estimating a mental state from such biological information.

A first problem is individual differences in biological reactions. Even if the accuracy of an operation remains substantially the same, or even if a degree of vigilance or concentration measured on the basis of an interview with a person remains substantially the same, how biological reactions appear greatly varies between individuals. A person's mental state cannot be correctly estimated by simply measuring biological information.

A second problem is stability. Even with the same subject, biological reactions might differ depending on an environment during measurement, a type of activity performed before the measurement, or an operation history. Even when a subjected is limited to a particular person, it is difficult to accurately estimate a mental state of the person only on the basis of biological reactions during measurement.

A third problem is an inspection method. A method is usually used in which certain stimuli are given to a subject and a mental state is estimated from biological reactions to the stimuli. In a laboratory, a certain task (e.g., mathematical calculations, quizzes, or direct stimuli to a body) can be assigned in a fixed environment and biological reactions to the certain task can be measured. During an actual operation, however, an operation environment and content of the operation can greatly vary. It is not easy to estimate a mental state of an operator in real-time under such a condition.

Figure 2:
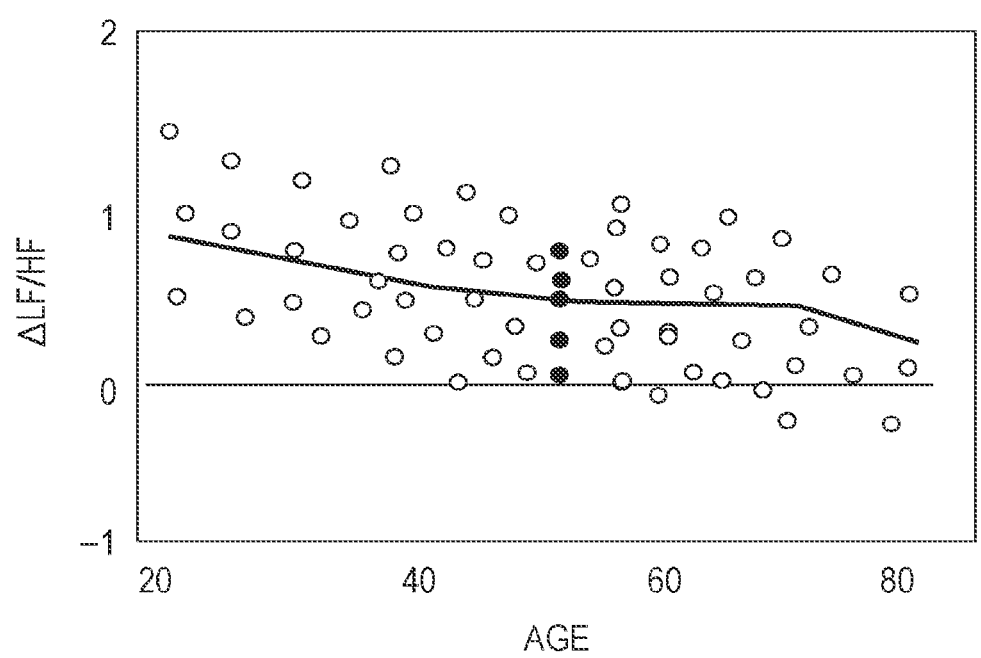
FIG. 2 is a diagram illustrating individual differences in biological reactions to stress.

FIG. 2 is a diagram illustrating individual differences in changes in biological information and variation between measurement operations at a time when a task was performed. Here, a calculation task was assigned to each subject, and a degree of stress caused by the task was measured on the basis of fluctuation in a heart rate while the subject was relaxed or performing the task. The stress at this time is also called "vigilance". A heart rate constantly fluctuates. A high-frequency component of the fluctuation in variation in the heart rate is said to be affected by the activity of a parasympathetic nervous system caused by respiration. A low-frequency component, on the other hand, is said to be affected by the activity of both a sympathetic nervous system and the parasympathetic nervous system. In this example, a range of the high-frequency component was equal to or higher than 0.20 Hz but lower than 0.35 Hz, and a range of the low-frequency component was equal to or higher than 0.05 Hz but lower than 0.20 Hz. A value indicating a ratio of the high-frequency component of fluctuation in the heart rate is denoted by HF, and a value indicating a ratio of the low-frequency component is denoted by LF. When a person is stressed or nervous, LF/HF increases. For this reason, this value can be used as an indicator of stress or nervousness.

ΔLF/HF of a vertical axis illustrated in FIG. 2 indicates the amount of change in LF/HF before and after a task is performed. Results illustrated in FIG. 2 indicate that ΔLF/HF exceeds zero (0) with some exceptions. It can be seen from these results that LF/HF tends to increase due to stress or nervousness. The amount of increase, however, becomes smaller as the age of a subject increases.

Solid circles in FIG. 2 indicate results of a plurality of tests conducted on the same person. It can be seen that variation between tests was great even with the same person.

The results illustrated in FIG. 2 were obtained under limited conditions, that is, obtained when a certain task was assigned to each subject. During an actual operation, however, content of an operation, that is, a task, is not constant. When content of an operation varies, biological information accordingly varies. It is therefore difficult to determine operation appropriateness of an operator during an actual operation only on the basis of measured values of biological information. The "operation appropriateness" refers to a degree of a mental state in which an operator can efficiently perform an operation without errors. Operation appropriateness refers to a degree of a mental state, such as vigilance, nervousness, attention, or concentration.

A system is possible in which an operator is asked to stop performing an operation and perform a certain judgment task and operation appropriateness is determined from a result of the judgment task. It is, however, not realistic to incorporate such a task during an actual operation. Such a system is therefore not widely used.

The present disclosure provides a novel technique for stably estimating a mental state of an operator during an operation. According to the embodiments of the present disclosure, an operation load is monitored and a relationship between the operation load and biological information is learned for each operator. By using data accumulated through a plurality of learning processes, changes in biological information caused by an operation can be estimated.

FIG. 1A is a diagram illustrating the configuration of an operation appropriateness determination system according to an exemplary embodiment of the present disclosure. An operation appropriateness determination system 100 includes an authentication apparatus 101, an operation sensing apparatus 102, a biometric sensing apparatus 106, a signal processing apparatus 108, a storage device 104, and a display apparatus 107. The signal processing apparatus 108 includes a biological information estimation unit 103 and an operation appropriateness determination unit 105.

In the present embodiment, persons are authenticated at beginnings of operations, and a database is built for each person. In the database, information indicating a load of each operation (referred to as "operation information" herein) and biological information obtained during the operation are associated with each other for the operation. The operation information may include content of the operation. By using stored data, an effect of individual differences in biological information can be reduced, and operation appropriateness can be stably determined regardless of the operator.

Personal authentication is performed, for example, when an operator inputs an operator identifier (ID) at a beginning of an operation or the authentication apparatus 101 performs biometric authentication. The biometric authentication can be performed, for example, using a method such as face recognition, fingerprint recognition, iris recognition, or vein recognition. In a mode in which the operator inputs a personal authentication code such as an operator ID, the authentication apparatus 101 can be an apparatus including an input device, such as a mobile information terminal or a personal computer (PC). The input device can include, for example, at least either a keyboard or a mouse. In a mode in which the authentication apparatus 101 performs biometric authentication, the authentication apparatus 101 is an apparatus having a function of performing biometric authentication such as face recognition, fingerprint recognition, iris recognition, or vein recognition. In the latter mode, the authentication apparatus 101 includes one or more biometric authentication devices necessary for personal authentication, such as a camera or a fingerprint sensor.

The operation sensing apparatus 102 monitors current operation conditions of an operator and outputs operation information indicating a load of an operation. The configuration of the operation sensing apparatus 102 varies depending on the content of the operation. If the operation is driving of a vehicle, for example, the operation sensing apparatus 102 can include a sensor such as an acceleration sensor or an angular velocity sensor. If the operation is office work or learning for which a computer is used, the operation sensing apparatus 102 can include the computer or an input device of the computer.

The biometric sensing apparatus 106 continuously or intermittently measures biological information regarding an operator during an operation. The biological information obtained by the biometric sensing apparatus 106 is biological information that has been actually measured. For this reason, the biological information will also be referred to as "measured biological information". The biometric sensing apparatus 106 may obtain biological information regarding an operator in a noncontact manner. When the biometric sensing apparatus 106 obtains biological information regarding an operator in a noncontact manner, the biological information can be obtained even if it is difficult for the operator to wear a device of a contact type because of the content of an operation. The use of the noncontact biometric sensing apparatus 106 also reduces awkwardness and uncomfortableness that would otherwise be caused by wearing of a biological sensor.

The storage device 104 stores measured biological information and obtained databases of operation information for different persons. In each database, data is accumulated for each person and for each operation. The storage device 104 can include a storage medium such as a flash memory, a magnetic disk, or an optical disc.

The signal processing apparatus 108 can be achieved, for example, by a digital signal processor (DSP), a programmable logical device (PLD) such as a field-programmable gate array (FPGA), or a combination of a central processing unit (CPU) and a computer program. The signal processing apparatus 108 may be a component of an external apparatus such as a server provided at a remote place. In this case, the external apparatus such as a server includes communication means and communicates data with the authentication apparatus 101, the operation sensing apparatus 102, the biometric sensing apparatus 106, the storage device 104, and the display apparatus 107.

The signal processing apparatus 108 includes the biological information estimation unit 103 and the operation appropriateness determination unit 105. These components can be achieved when the signal processing apparatus 108 has executed a computer program stored in the storage device 104. Alternatively, these components may be discrete circuits configured to perform operations that will be described hereinafter.

The biological information estimation unit 103 estimates current biological information regarding an operator on the basis of the data accumulated in the storage device 104. The estimated biological information is a value of current biological information estimated on the basis of operation loads and biological information regarding the operator obtained in the past. For this reason, this information will be referred to as "estimated biological information". The operation appropriateness determination unit 105 compares estimated biological information and measured biological information regarding an operator with each other and determines operation appropriateness on the basis of a result of the comparison. A specific example of a process performed by the biological information estimation unit 103 and the operation appropriateness determination unit 105 will be described later.

If there is no abnormality in an operator, estimated biological information based on past data substantially matches measured current biological information. If there is an abnormality in an operator, on the other hand, a change larger than a value of variation calculated from past data is caused between estimated biological information and measured biological information. In this case, the operation appropriateness determination unit 105 determines that operation appropriateness is not enough. In this case, the operation appropriateness determination unit 105 causes the display apparatus 107 to display an advice, a warning, or the like to the operator. Alternatively, the operation appropriateness determination unit 105 may forcibly stop the operation. Forcible stopping of an operation is a process for stopping an apparatus or a system. Alternatively, a speaker may be provided instead of, or in addition to, the display apparatus 107, and the operation appropriateness determination unit 105 may cause the speaker to output a sound of an alert or an advice.

Next, an example of the overall operation of the operation appropriateness determination system will be described with reference to FIG. 1B.

FIG. 1B is a flowchart illustrating an example of the operation of the operation appropriateness determination system. The system performs the operation illustrated in FIG. 1B for each operation.

First, in step S101, the authentication apparatus 101 identifies an operator. The authentication apparatus 101 identifies an operator using a method such as, as described above, an input operation performed by the operator or biometric authentication.

In step S102, the biometric sensing apparatus 106 obtains biological information regarding the operator. The biometric sensing apparatus 106 can obtain biological information using, for example, a noncontact CBF measuring apparatus, which will be described later. The obtained biological information can be, for example, information indicating temporal changes in the operator's CBF or information indicating temporal changes in the operator's heart rate.

In step S103, the operation sensing apparatus 102 detects the content of an operation currently performed by the operator and outputs information indicating the content of the operation. The operation sensing apparatus 102 may also calculate a value indicating a load of the operation. An apparatus other than the operation sensing apparatus 102, namely a processor of the signal processing apparatus 108, for example, may calculate the load of the operation, instead.

In step S104, the signal processing apparatus 108 stores the measured biological information, the information indicating the load of the operation, and time information in the storage device 104 for each operator while associating the measured biological information, the information indicating the load of the operation, and the time information with one another.

In step S106, the signal processing apparatus 108 compares estimated biological information and the measured biological information regarding the operator with each other. Next, in step S107, the signal processing apparatus 108 determines the operation appropriateness of the operator on the basis of a result of the comparison. If a difference between a value of the estimated biological information and a value of the measured biological information exceeds a certain threshold, for example, it can be determined that the operation is not appropriate. Alternatively, the operation appropriateness may be determined stepwise in accordance with the difference between the value of the estimated biological information and the value of the measured biological information.

If it is determined that the operator is not appropriate for the operator, the signal processing apparatus 108 proceeds to step S108. In step S108, as described above, the signal processing apparatus 108 advises or warns the operator or forcibly stops the operation through another apparatus such as the display apparatus 107.

The operations in steps S102 to S108 can be repeatedly performed at certain time intervals, for example, while the operator is performing the operation. When an operation has been completed and the same operation is performed again, data stored in the past is used in step S105. By using data accumulated for a relatively long period of time, more accurate estimation can be performed.

Especially important points in the embodiment of the present disclosure are as follows.

(1) Operation information indicating a load of an operation and biological information are accumulated in a database for each person for a relatively long period of time. Data can be repeatedly accumulated for each operation for a period of time such as several days, one week, one month, several months, half a year, one year, or several years.

(2) Current biological information is estimated on the basis of accumulated data.

(3) The estimated current biological information and measured biological information, which has been actually measured, are compared with each other, and operation appropriateness at a present time is determined.

In the present embodiment, a mechanism with which current biological information can be estimated in real-time by learning changes in an operation load and changes in biological information is constructed. As a result, a load on an operator can be estimated more accurately.

A conventional system exists in which a database of biological information for each person is constructed in order to correct individual differences and operation appropriateness of an operator is determined while correcting individual differences. With a certain operation in a test environment, that is, with a test in which an operator performs a test task and a reaction is observed, effectiveness of such a system has been verified. For example, a method is known in which a test task in which an operator does mathematical calculations or recollects related words is assigned to the operator and the operator's CBF is measured. In an actual operation environment, however, it is difficult to assign such an operation task during work, learning, or driving. An operator's mental state needs to be determined from changes in biological information during operations whose loads vary. By a simple method, such as one in which past data is simply averaged or data obtained under similar conditions is extracted and averaged, however, an effect of individual differences or an operation load cannot be corrected.

In the embodiment of the present disclosure, a relationship between operation loads and biological reactions for each person is obtained from past data regarding measured values of the operation loads of actual operations and biological information. A current mental state or operation appropriateness of an operator is estimated from the relationship between operation loads and biological reactions. A biggest difference from the conventional system is that correlation between operation loads and biological information for each person is obtained from past measured data and current biological information is estimated on the basis of the correlation.

Next, an example of a method for measuring biological information will be described.

In the present embodiment, a stable, accurate biometric apparatus is used to stably determine a mental state. When biological information is constantly measured during an operation, a sensor in contact with an operator's body might obstruct the operation. In addition, a contact state of a contact sensor might change due to motion of an operator's body during an operation, thereby decreasing measuring accuracy. In view of these problems, the noncontact biometric sensing apparatus 106 based on an imaging device is used in the embodiment illustrated in FIG. 1A. By using the imaging device, noncontact biometric sensing, which does not cause awkwardness, can be achieved. In addition, the imaging device includes a large number of pixels arranged in two dimensions and is capable of obtaining a large number of pieces of biological information at once. Accuracy can therefore be increased through a process such as averaging of signals from a plurality of pixels. Furthermore, the imaging device obtains a two-dimensional image signal. Information regarding differences between biological reactions of different body parts can be obtained from the two-dimensional image signal, which is highly advantageous. It is known, for example, that nasal blood flow decreases due to psychological stress and accordingly nose temperature decrease. When the imaging device is used, nasal blood flow and forehead blood flow, which is to be compared with the nasal blood flow, can be simultaneously measured. Changes in biological information can therefore be stably measured.

Whereas the method for obtaining biological information employing an imaging device has various advantages as described above, there is also a problem. That is, it is difficult to obtain information regarding an inside of a body, which is necessary to determine a state of brain activity. This is because if an image of a translucent subject such as a living body is captured, most of information is about light reflected from a surface of the body, and light from the inside of the living body is buried. Near-infrared light is more penetrating to a human body than visible light and suitable for obtaining information regarding a deep part of a living body. Even if near-infrared light is used, however, more light reflected from a surface of a living body or the skin than light reflected from an inside of the living body is obtained. As a result, a signal-to-noise ratio decreases, and accurate measurement cannot be stably performed.

In order to increase a ratio of light reflected from an inside of a living body including biological information and stably obtain the biological information, light emitted from a light source may be modulated temporally or spatially. With such a configuration, optical signals from a deeper part of a living body can be selectively obtained.

Figure 3A:
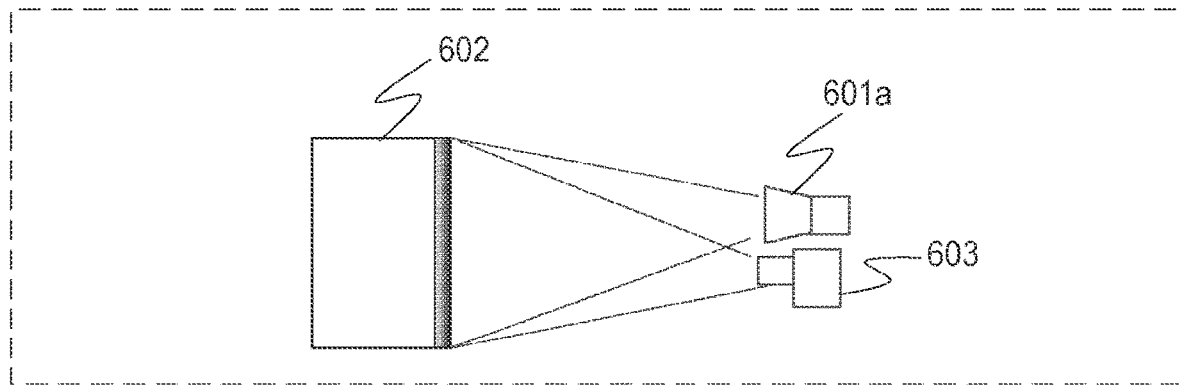
FIG. 3A is a diagram illustrating an imaging device for which a light source that emits light having a uniform distribution is used.
Figure 3B:
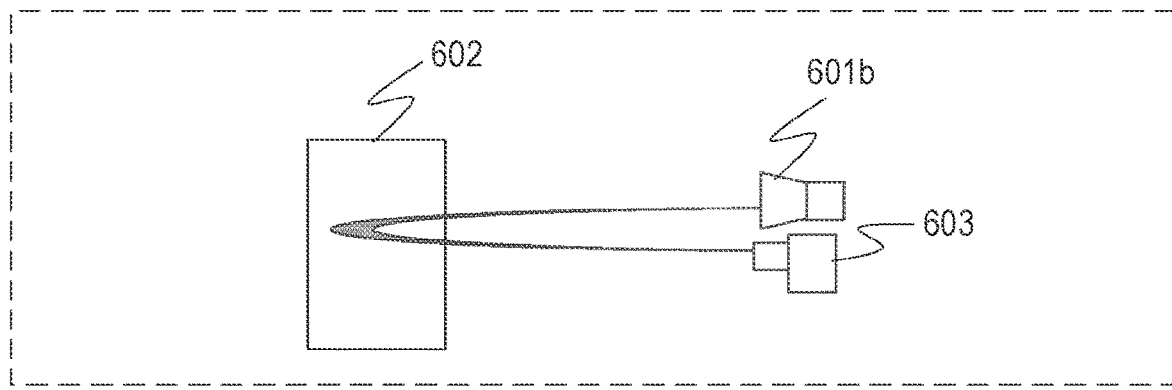
FIG. 3B is a diagram illustrating a concept of an imaging device for which a light source that emits temporally modulated light is used.
Figure 3C:
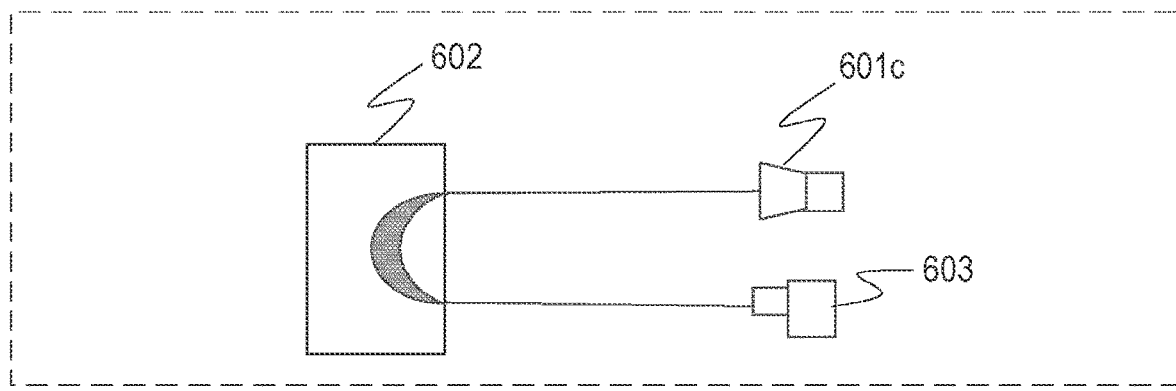
FIG. 3C is a diagram illustrating a concept of an imaging device for which a light source that emits spatially modulated light is used.

FIG. 3A is a diagram schematically illustrating an imaging method employing a light source that emits light having a uniform distribution. FIG. 3B is a diagram schematically illustrating an imaging method employing a light source that emits temporally modulated light. FIG. 3C is a diagram schematically illustrating an imaging method employing a light source that emits spatially modulated light.

In the example illustrated in FIG. 3A, a light source 601a emits light having a uniform distribution. When the light source 601a illuminates a living body 602 and an image of the living body 602 is captured, most of signals obtained by an imaging device 603 is a component corresponding to light reflected from a surface of the living body 602. Since a ratio of a component corresponding to light from an inside of the living body 602 is too low to achieve sufficient accuracy.

In the example illustrated in FIG. 3B, on the other hand, a light source 601b emits light subjected to temporal modulation. The light source 601b illuminates the living body 602, and a timing at which the imaging device 603 captures an image is controlled in synchronization with the modulation of light from the light source 601b. In this case, time taken until detection of light after emission of the light can be changed by controlling a light emission time and a timing of imaging. The time taken until detection of light after emission of the light depends on a distance over which the light propagates from the light source 601b to the imaging device 603 via the living body 602. By appropriately controlling the timings of emission of light and detection of the light, reflected light having information at any depth can be detected. By this method, reflected light having information at any depth of a living body can be selectively detected. As a result, biological information can be detected with a high signal-to-noise ratio.

In the example illustrated in FIG. 3C, a light source 601c emits spatially modulated light. The light emitted from the light source 601c is radiated onto the living body 602, and the imaging device 603 obtains signals from an area outside a radiated part. If a position of the light source 601c and a detection position are far from each other, the light reaches the detection position while forming an optical path having an arched shape called a "banana shape". Detected signals include information regarding light that has passed through a deeper part of the living body 602 than when the light source 601a that emits uniform light illustrated in FIG. 3A is used. The method employing the light source 601c is thus suitable for obtaining information regarding a deep part of a living body.

Information regarding a deeper part of a living body can thus be obtained by using a light source that emits temporally modulated light or spatially modulated light and an imaging method that suits the light source.

In an embodiment of the present disclosure, a system is designed on the basis of the following new pieces of knowledge.

Use of biological information estimated from a database in which a relationship between biological information and operation loads is stored is effective in constructing a practical operation appropriateness determination system while reducing an effect of individual differences in biological reactions Use of an imaging device including a light source that emits temporally or spatially modulated near-infrared light is effective in improving accuracy of obtaining of biological information Here, near-infrared light, that is, near-infrared radiation, refers to electromagnetic waves whose wavelengths under vacuum are 700 nm to 2,500 nm. The embodiments of the present disclosure are not limited to a mode in which near-infrared light is used. By using near-infrared light, however, biological signals can be obtained more accurately.

The embodiments of the present disclosure will be described hereinafter more specifically. Description unnecessarily detailed, however, might be omitted. For example, detailed description of well-known facts and redundant description of substantially the same components might be omitted. This is in order to prevent the following description from becoming unnecessarily redundant and facilitate understanding of those skilled in the art. The inventor provides the accompanying drawings and the following description in order for those skilled in the art to sufficiently understand the present disclosure and does not intend to limit the theme described in the claims.

First Embodiment

An operation appropriateness determination system employing a noncontact CBF measuring apparatus will be described as a first embodiment. In the present embodiment, operation appropriateness is determined from information regarding changes in an operator's CBF. The present embodiment is an example in which the operation appropriateness determination system is used to monitor a driver. A target operation is driving of a vehicle, and the operator is a driver.

CBF measuring apparatuses that measure changes in CBF using near-infrared light have already been proposed. In a conventional method, an operator alternates between a predetermined certain task and a break a plurality of times. The certain task is, for example, calculation, memorization, association, quizzes, or the like. The CBF measuring apparatuses measure changes in CBF in different periods. A level of brain activity can be estimated from data obtained as a result of the measurement. It is, however, not realistic to repeat such a fixed task during driving.

In the present embodiment, a driving operation, which is not a fixed operation, is used as a task instead of a fixed task. Changes in CBF are measured during the driving operation. A surrounding environment constantly changes during a driving operation. That is, a driving operation can be a constantly changing operation. In the present embodiment, an operation load is estimated on the basis of information obtained by an acceleration sensor. According to the present embodiment, a driving operation, which is a daily operation, can serve as a task instead of a fixed task. In other words, according to the present embodiment, "taskless CBF measurement" can be performed.

Figure 4A:
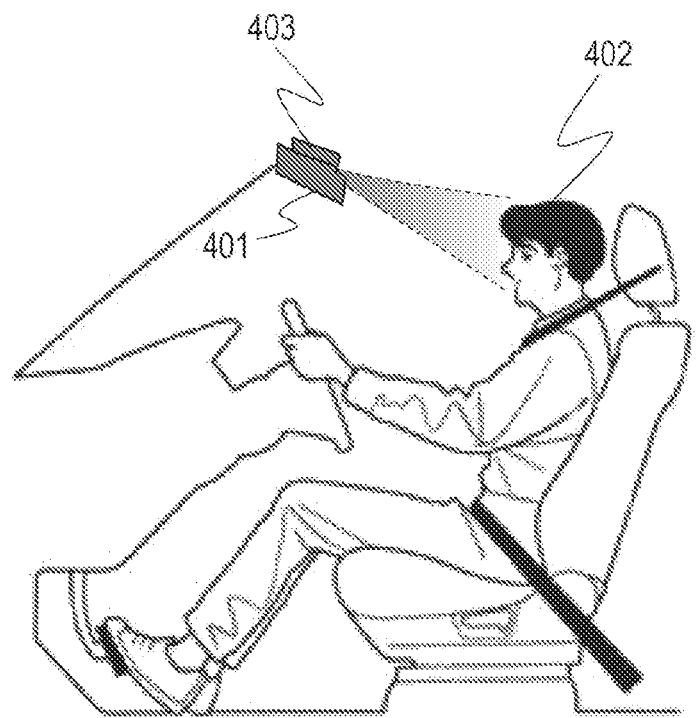
FIG. 4A is a diagram illustrating an example of arrangement of an operation appropriateness determination system according to a first embodiment of the present disclosure.

FIG. 4A is a diagram illustrating an example of the configuration of the operation appropriateness determination system according to the first embodiment of the present disclosure. As illustrated in FIG. 4A, the operation appropriateness determination includes a CBF measuring apparatus 401 and an acceleration sensor 403. The CBF measuring apparatus 401 is an example of the above-described biometric sensing apparatus. The acceleration sensor 403 is an example of the above-described operation sensing apparatus. The CBF measuring apparatus 401 measures CBF of a driver 402. The CBF measuring apparatus 401 is provided in an upper part of a vehicle in order not to enter a field of vision of the driver 402 in a direction of a windshield on a driver's sheet side. The acceleration sensor 403 is provided adjacent to the CBF measuring apparatus 401. The acceleration sensor 403 monitors conditions of a driving operation.

Figure 4B:
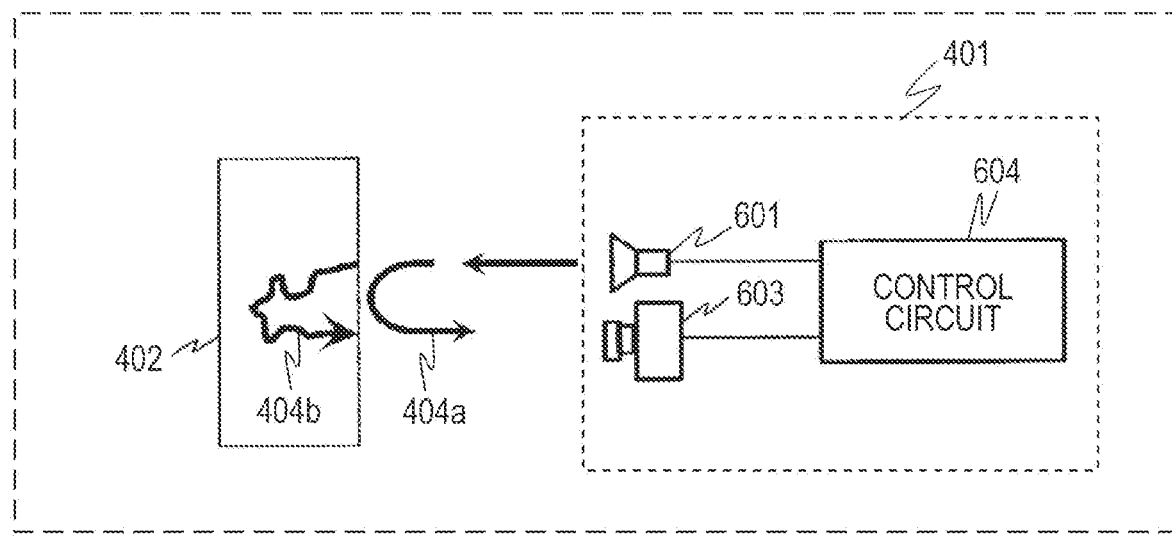
FIG. 4B is a diagram illustrating an outline of a cerebral blood flow measuring apparatus according to the first embodiment of the present disclosure.

The configuration of the CBF measuring apparatus 401 will be described with reference to FIG. 4B. FIG. 4B is a diagram illustrating the schematic configuration of the CBF measuring apparatus 401 according to the first embodiment of the present disclosure. The CBF measuring apparatus 401 includes a light source 601, the imaging device 603, and a control circuit 604. The control circuit 604 is connected to the light source 601 and the imaging device 603. The control circuit 604 controls the light source 601 and the imaging device 603.

The CBF measuring apparatus 401 measures the CBF of the driver 402 in a noncontact manner using the imaging device 603 of a time-of-flight (TOF) type. The light source 601 emits temporally modulated light in accordance with an instruction from the control circuit 604. The imaging device 603 captures an image in accordance with an instruction from the control circuit 604 in synchronization with the emission of light from the light source 601. The imaging device 603 captures an image of a forehead of the driver 402, which is a part to be measured. The imaging device 603 includes at least one charge accumulation unit that receives light and that accumulates signal charge. The imaging device 603 typically includes a plurality of charge accumulation units arranged in two dimensions. As a result, a two-dimensional image signal can be obtained.

The light source 601 according to the present embodiment is a light source that emits pulsed near-infrared light having wavelengths of 750 nm and 850 nm. The light source 601 irradiates the forehead of the driver 402 with these two types of near-infrared light. The light source 601 can be, for example, a laser light source.

The imaging device 603 according to the present embodiment includes an image sensor including a plurality of light receiving elements arranged in two dimensions. Each light receiving element is sensitive to the infrared light having the two wavelengths. The imaging device 603 therefore obtains two-dimensional images based on the two types of infrared light radiated onto the forehead of the driver 402.

The control circuit 604 can measure a distance to a target part on the basis of time taken for pulsed light emitted from the light source 601 to be reflected and reach the imaging device 603. The control circuit 604 temporally decomposes an optical signal returning from the forehead to measure the intensity of an optical component 404a reflected from a surface of the forehead and the intensity of an optical component 404b that has reached a brain of the driver 402 and returned. For example, the control circuit 604 measures the intensity of the two optical components 404a and 404b by controlling a timing of an electronic shutter of the imaging device 603. Changes in the concentration of oxygenated hemoglobin ($HbO_2$) and the concentration of deoxygenated hemoglobin (Hb) in cerebral blood can be measured on the basis of the intensity of the two types of light. The CBF measuring apparatus 401 thus measures changes in the concentration of oxygenated hemoglobin and deoxygenated hemoglobin in the brain using the light source 601 that emits the light having the two wavelengths. As a result, operation appropriateness of the driver 402 during driving can be determined.

A major role of blood is to receive oxygen from lungs, carry the oxygen to tissues, receive carbon dioxide from the tissues, and carry the carbon oxygen to the lungs. About 15 g of hemoglobin exists in 100 ml of blood. Hemoglobin bonded with oxygen is called "oxygenated hemoglobin", and hemoglobin not bonded with oxygen is called "deoxygenated hemoglobin". Optical absorption properties are different between oxygenated hemoglobin and deoxygenated hemoglobin. Oxygenated hemoglobin absorbs near-infrared radiation having wavelengths longer than about 830 nm relatively well. Deoxygenated hemoglobin, on the other hand, absorbs red light and near-infrared radiation having wavelengths shorter than 830 nm relatively well. Absorptance of near-infrared radiation at a wavelength of 830 nm is the same between oxygenated hemoglobin and deoxygenated hemoglobin. A ratio of the two types of hemoglobin or an oxygen saturation level can be obtained from a ratio of the intensity of infrared light to the intensity of red light. An oxygen saturation level is a value indicating the percentage of hemoglobin in blood bonded with oxygen. The oxygen saturation level is defined by the following expression.

$$\text{Oxygen saturation level} = C(HbO_2)/[C(HbO_2)+C(Hb)] \times 100(\%)$$

Here, C(Hb) denotes the concentration of deoxygenated hemoglobin, and $C(HbO_2)$ denotes the concentration of oxygenated hemoglobin.

A living body includes components other than blood that absorb light having wavelengths of red and near infrared. Temporal variation in optical absorptance mainly depends on hemoglobin in arterial blood. Changes in the concentration of the two types of hemoglobin and/or a blood oxygen saturation level can therefore be measured on the basis of variation in absorptance. Arterial blood ejected from a heart moves through blood vessels as pulse waves. Venous blood, on the other hand, does not have pulse waves. Light incident on a living body passes through the living body while being absorbed in different layers of the living body, such as arteries, veins, and tissues other than blood. At this time, tissues other than the arteries do not vary in thickness over time. Light scattered inside the living body, therefore, changes in intensity over time in accordance with changes in the thickness of an artery blood layer due to pulsation. The changes in the scattered light reflect the changes in the thickness of the artery blood layer and are not affected by venous blood and tissues. Information regarding arterial blood can therefore be obtained by focusing upon only a varying component of scattered light. Pulsation can also be obtained by measuring a cycle of the component that changes over time.

It is to be noted that the light source 601 that emits the light having the two wavelengths need not necessarily be used. For example, if the concentration of oxygenated hemoglobin alone is measured, for example, a light source that emits near-infrared light having a single wavelength longer than 830 nm may be used, instead.

Figure 5:
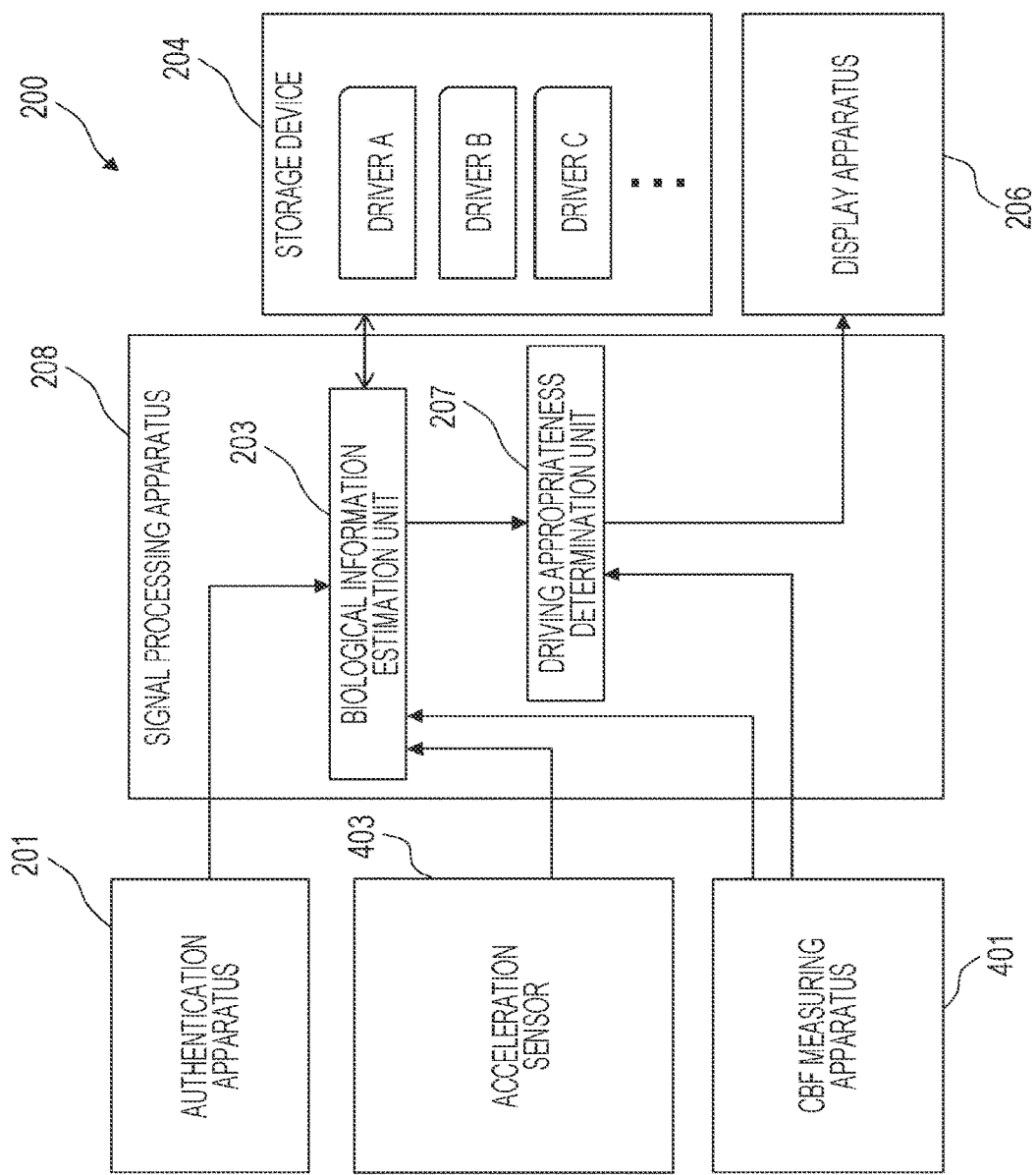
FIG. 5 is a diagram illustrating the configuration of the operation appropriateness determination system according to the first embodiment of the present disclosure.

FIG. 5 is a diagram illustrating the configuration of an operation appropriateness determination system 200 according to the first embodiment of the present disclosure. The operation appropriateness determination system 200 includes an authentication apparatus 201, a signal processing apparatus 208, a storage device 204, and a display apparatus 206 in addition to the acceleration sensor 403 and the CBF measuring apparatus 401. The signal processing apparatus 208 includes a biological information estimation unit 203 and a driving appropriateness determination unit 207. As described above, the acceleration sensor 403 functions as an operation sensing apparatus, and the CBF measuring apparatus 401 functions as the biometric sensing apparatus.

The authentication apparatus 201 authenticates a driver, who is an operator. The authentication apparatus 201 includes an imaging device. The imaging device obtains an image of the driver's face at a beginning of driving. The driver is identified by comparing the face image with a face image stored in the storage device 204 in advance.

The imaging device of the authentication apparatus 201 may be the imaging device 603 of the CBF measuring apparatus 401. In this case, the CBF measuring apparatus 401 also identifies the driver through face recognition using an image for CBF measurement. The CBF measuring apparatus 401 has a function of a camera. An image based on the optical component 404a reflected from a surface of the driver's face is similar to an image obtained by a common camera. Personal authentication, therefore, can be easily performed using an image output from the CBF measuring apparatus 401. A single apparatus may thus have a function of an authentication apparatus and a function of a biometric sensing apparatus.

The acceleration sensor 403 monitors current driving conditions and measures an operation load on the driver 402. The acceleration sensor 403 can monitor not only degrees of acceleration and deceleration during driving but also an integral of acceleration, which indicates a driving speed, lateral acceleration, which indicates a cornering speed at a curve, and periodic variation in lateral acceleration, which indicates wandering of a vehicle. The acceleration sensor 403 is therefore effective in detecting conditions of a driving operation performed by the driver 402.

It is possible to obtain driving information regarding the vehicle from the vehicle in order to detect driving conditions. The "driving information" refers to information regarding temporal changes in a driving operation, such as acceleration, braking, and steering. The driving information is an example of the above-described operation information. The operation appropriateness determination system 200 may include a communication circuit in order to communicate data with the vehicle. In such a system, not the acceleration sensor 403 but a computer inside the vehicle functions as the operation sensing apparatus. When the acceleration sensor 403 is used as in the present embodiment, the system can be constructed at low cost. In addition, the system can be constructed simply without integrating different pieces of information for different vehicle models. If information communication for automobiles will develop and vehicle information can be obtained more easily, driving information can be received from a vehicle more easily without providing the acceleration sensor 403 in the operation appropriateness determination system 200.

A method for detecting driving conditions on the basis of an output of the acceleration sensor 403 and obtaining a driving load, that is, an operation load, will be described hereinafter.

As described above, the acceleration sensor 403 can monitor various driving conditions during driving, such as acceleration, deceleration, driving speed, cornering speed, and wandering of the vehicle. A driving load can be calculated on the basis of at least one of these pieces of information. The driving load increases as acceleration or deceleration increases, vehicle screed increases, or cornering speed increases. Keeping a vehicle stable within a lane also increases the driving load. Wandering of a vehicle indicates that the vehicle is not kept stable within a lane. Wandering of a vehicle itself, therefore, is an important indicator in terms of driving appropriateness. Wandering of a vehicle can be detected from small periodic changes in lateral acceleration. In calculation of a driving load, wandering decreases the driving load. This is because stably controlling a vehicle causes a great driving load. Now, acceleration of a vehicle is denoted by $\alpha$, lateral acceleration is denoted by $\beta$, and a gentle periodic variation component of the lateral acceleration is denoted by $\gamma$. A driving load $L(t)$ is represented by expression (1).

$$L(t)=k_1|\alpha(t)|+k2\int\alpha(t)dt+k_3|\beta(t)|+k_4|\gamma(t)| \quad (1)$$

Here, $k_1$ to $k_4$ are constants, and $\int\alpha(t)dt$ denotes a vehicle speed. Appropriate values are set to the constants $k_1$ to $k_4$ in advance on the basis of, for example, an experiment.

Figure 6:
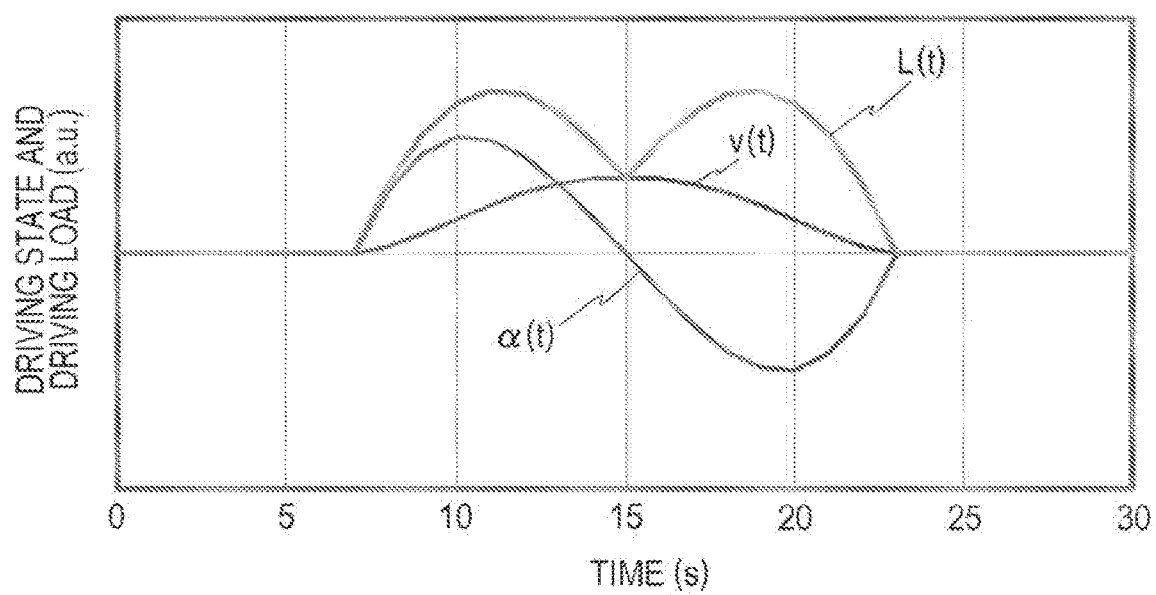
FIG. 6 is a diagram illustrating an example of calculation of an operation load of driving.

FIG. 6 illustrates an example of a result of calculation of an acceleration $\alpha(t)$, a velocity $v(t)$, and the driving load $L(t)$ at a time when driving operations, namely acceleration and deceleration, have been performed. The driving load $L(t)$ can be easily calculated on the basis of expression (1) from data obtained by the acceleration sensor 403. The driving load $L(t)$ can be calculated by a processor incorporated into or connected to the acceleration sensor 403. The signal processing apparatus 208 may calculate the driving load $L(t)$, instead.

The CBF measuring apparatus 401 continuously or intermittently measures the CBF of the driver 402 in a noncontact manner using the above-described method.

Figure 7:
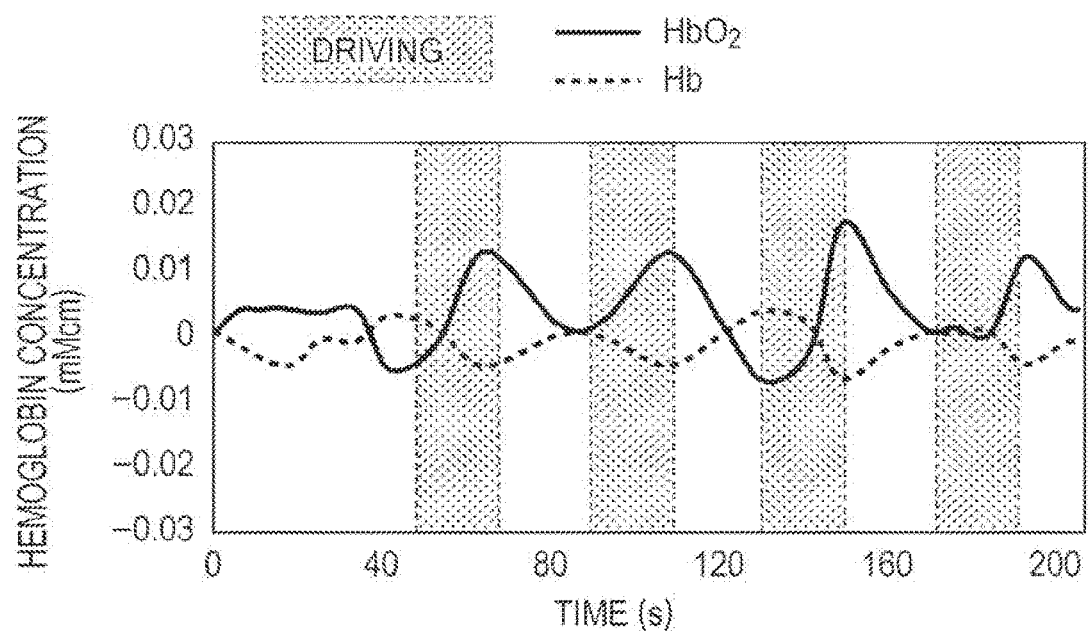
FIG. 7 is a diagram illustrating measured values of changes in cerebral blood flow during a driving task.

FIG. 7 illustrates an example of measured values of changes in a driver's CBF at a time when a driving test of a vehicle was performed in a test course. The driver performed a driving task in which acceleration, deceleration, and stopping were repeated at a cycle of 40 seconds. Hatched sections indicate periods in which acceleration or deceleration was performed, and white sections indicate periods in which the vehicle was stationary. It can be seen that the concentration of oxygenated hemoglobin ($HbO_2$) in the driver's CBF increased and the concentration of deoxygenated hemoglobin (Hb) decreased because of the driving operation, namely acceleration or deceleration. It can also be seen that there were delays in changes in CBF relative to the driving operations. This behavior of the changes in CBF is considered to occur due to the following mechanism.

First, local neural activity occurs in the frontal lobe due to a driving operation, and the amount of oxygen consumed by brain cells increases. In order to supply oxygen to the brain cells, local blood flow in surrounding capillaries increases. At this time, the increase (about 30% to 50%) in blood flow for supplying oxygen is larger than the increase (about 5%) in the amount of oxygen actually consumed. Blood flow and a flow rate increase in the capillaries and venules. Oxygenated hemoglobin rapidly flows, thereby increasing the concentration of oxygenated hemoglobin and decreasing the concentration of deoxygenated hemoglobin. This is the mechanism of increasing the concentration of oxygenated hemoglobin and decreasing the concentration of deoxygenated hemoglobin. It is to be noted that since blood flow increases after brain activity and consumption of oxygen, a change in CBF occurs after the brain activity. As can be seen from FIG. 7, the changes in CBF occurred with delays of several seconds after the brain activity for the driving operations. The delays are important in estimating a current CBF.

The signal processing apparatus 208 accumulates biological information and a driving load obtained for each person in the storage device 204 to construct a database. The biological information estimation unit 203 of the signal processing apparatus 208 estimates current biological information from the accumulated data. The estimated biological information is a value of the current biological information estimated from past driving loads and biological information regarding the driver 402, who is the operator. The operation of the biological information estimation unit 203 will be described in more detail.

An estimated value of a change in CBF can be calculated by performing convolution integration on a hemodynamic response function (HRF) and an operation load obtained from data obtained by the acceleration sensor 403. The HRF is a function indicating a temporal change in changes in CBF caused by brain activity. A mathematical expression for the amount of change in CBF is, for example, expression (2).

$$HRF_i(t)*L_i(t)=\Delta HbO_i(t) \quad (2)$$

Here, $HRF_i(t)$ denotes the HRF of a driver i, $L_i(t)$ denotes the operation load on the driver i, and $\Delta HbO_i(t)$ denotes the estimated amount of change in the concentration of oxygenated hemoglobin of the driver i. A sign "*" denotes the convolution integration. The CBF measuring apparatus 401 according to the present embodiment can measure both the concentration of oxygenated hemoglobin and the concentration of deoxygenated hemoglobin. In this example, however, only changes in the concentration of oxygenated hemoglobin are used as the amount of change in CBF due to brain activity. This is because, as illustrated in FIG. 7, the concentration of oxygenated hemoglobin and the concentration of deoxygenated hemoglobin change in a symmetrical manner, and the amount of change in the concentration of oxygenated hemoglobin is larger.

The concentration of deoxygenated hemoglobin, however, can be used, for example, to detect an abnormality in measured data. As described above, the concentration of oxygenated hemoglobin and the concentration of deoxygenated hemoglobin change in a symmetrical manner as long as measurement is performed correctly. If a certain disturbance, namely variation in radiated light or a bodily motion, for example, occurs, the concentration of oxygenated hemoglobin and the concentration of deoxygenated hemoglobin can change in the same direction. An abnormality in measurement can be easily detected by monitoring the concentration of deoxygenated hemoglobin, and abnormal data can be removed. It is important to note that the HRF $HRF_i(t)$ and the operation load $L_i(t)$ change over time.

The HRF $HRF_i(t)$ can be approximated by a function indicated in expression (3).

$$HRF_i(t)=A_o((t-\delta)/\tau)^2 \exp(-((t-\delta)/\tau)^2) \quad (3)$$

Variables $A_o$, $\delta$, and $\tau$ in this expression and $k_1$ to $k_4$ in expression (1) representing the operation load $L_i(t)$ can be constantly recalculated from results of measurement.

Figure 8A:
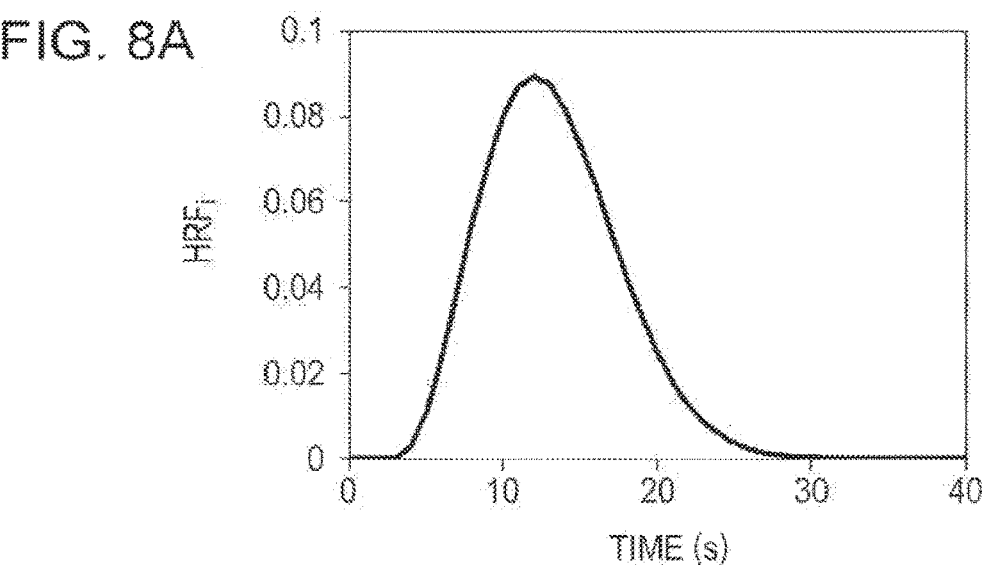
FIG. 8A is a first diagram illustrating a method for estimating cerebral blood flow.
Figure 8B:
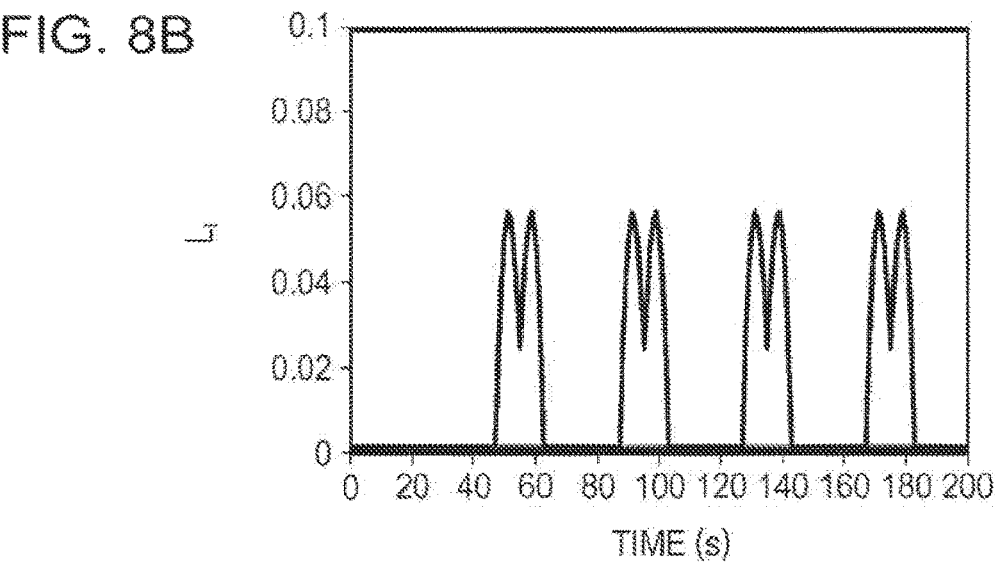
FIG. 8B is a second diagram illustrating the method for estimating cerebral blood flow.
Figure 8C:
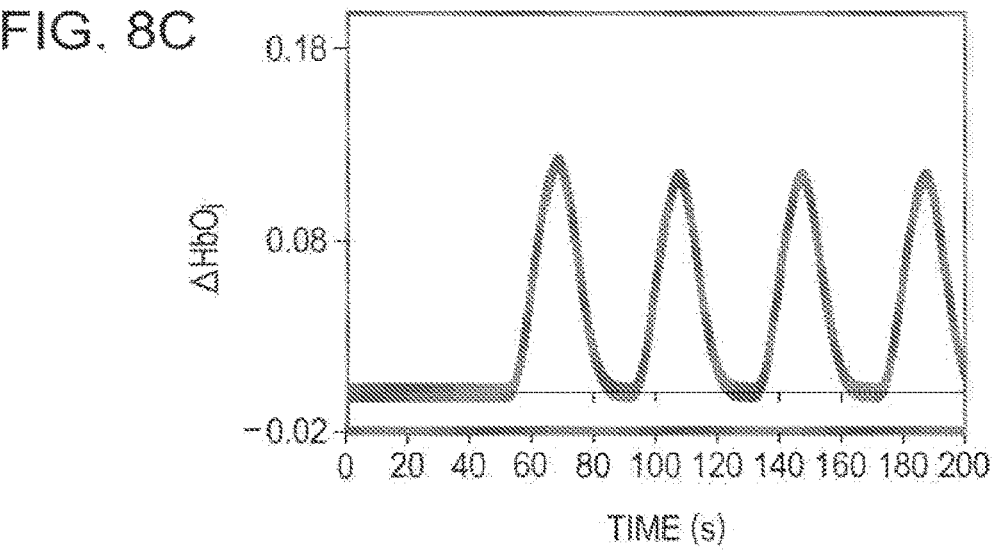
FIG. 8C is a third diagram illustrating the method for estimating cerebral blood flow.

FIG. 8A is a diagram illustrating an example of the HRF $HRF_i(t)$. FIG. 8B is a diagram illustrating an example of the operation load $L_i(t)$. FIG. 8C is a diagram illustrating an example of the amount $\Delta HbO_i(t)$ of change in the concentration of oxygenated hemoglobin.

The amount $\Delta HbOi(t)$ of change in the concentration of oxygenated hemoglobin illustrated in FIG. 8C is calculated using the method indicated by expression (2) and the functions illustrated in FIGS. 8A and 8B. Parameters Ao, $\delta$, $\tau$, and k1 to k4 are optimized such that a calculated $\Delta HbOi$ and $\Delta HbOm$, which denotes the measured amount of change in the concentration of oxygenated hemoglobin, match. Not only current data but also chronological data weighted in a time direction is used for the calculation. A multivariate analysis is used to determine the parameters. Alternatively, the parameters can be determined accurately through machine learning. The signal processing apparatus 208 learns and optimizes an expression for estimating biological information in real-time from a database of biological information and driving loads for each person accumulated in the storage device 204. As a result, operation appropriateness of a driver can be accurately determined. An effect of individual differences can be removed by creating a database for each person, and changes in a person's biological information can be accurately estimated by accumulating personal data. In addition, by calculating a load during driving on the basis of data from the acceleration sensor 403, changes in the biological information due to an operation that changes over time or driving conditions can be estimated.

Figure 9A:
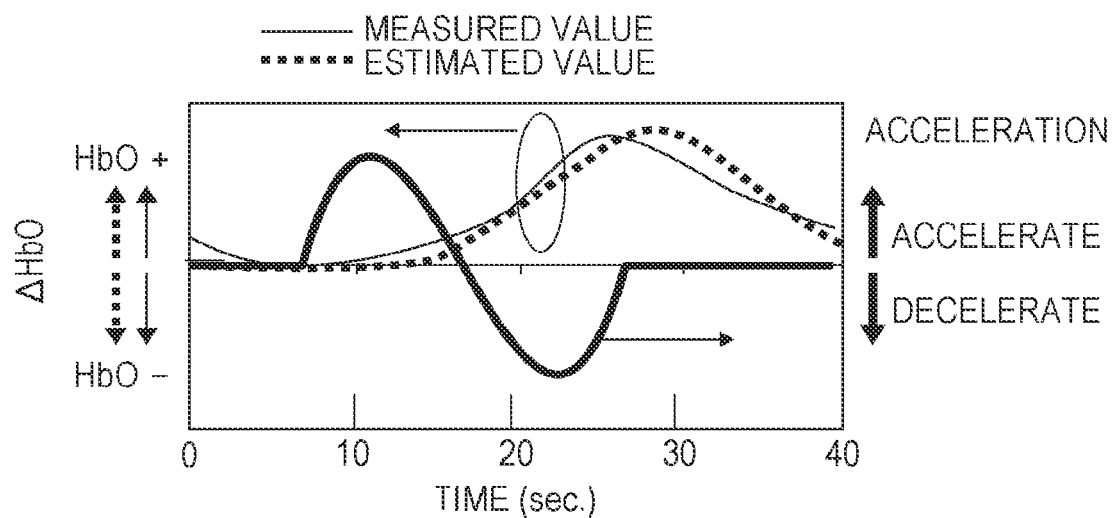
FIG. 9A is a diagram illustrating estimated changes in cerebral blood flow and measured changes in cerebral blood flow during normal driving.
Figure 9B:
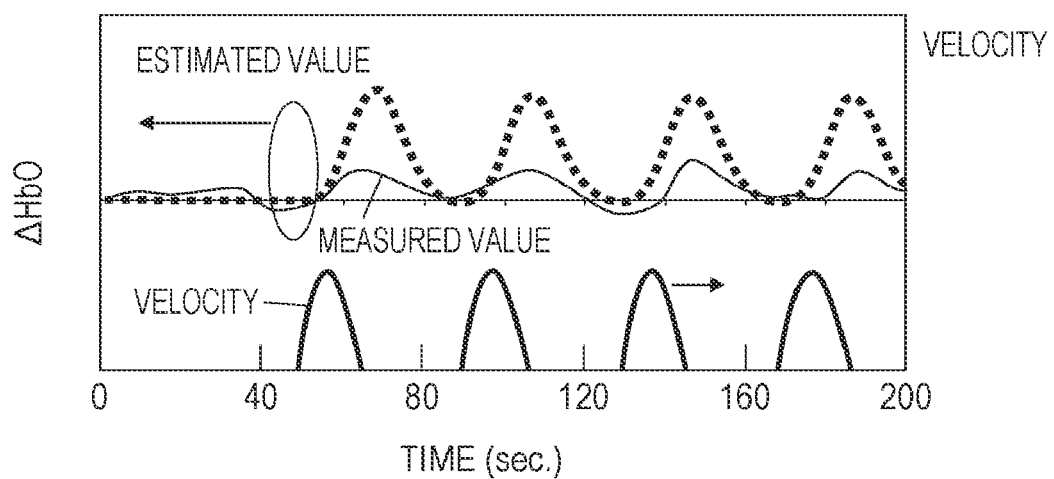
FIG. 9B is a diagram illustrating estimated changes in cerebral blood flow and measured changes in cerebral blood flow in a state without driving appropriateness.

FIG. 9A is a diagram illustrating estimated values (broken line) and measured values (solid line) of changes in CBF during normal driving. FIG. 9B is a diagram illustrating estimated values (broken line) and measured values (solid line) of changes in CBF in a state without driving appropriateness. The changes in CBF here are changes in the concentration of oxygenated hemoglobin. A vertical axis in a left part of FIG. 9A represents change ($\Delta HbO$) in the concentration of oxygenated hemoglobin, and a vertical axis in a right part of FIG. 9A represents acceleration. A vertical axis in a left part of FIG. 9B represents change ($\Delta HbO$) in the concentration of oxygenated hemoglobin, and a vertical axis in a right part of FIG. 9B represents velocity. Changes in CBF are observed after corresponding driving operations such acceleration and deceleration.

The driving appropriateness determination unit 207 compares estimated biological information and actually measured biological information with each other. If there is no problem in driving appropriateness of a driver, current changes in CBF estimated from a database and measured changes in CBF substantially match as illustrated in FIG. 9A. If there is an abnormality in the driver, on the other hand, a difference larger than a variation calculated from past data is caused between the estimated value and the measured value of biological information as illustrated in FIG. 9B. In the example illustrated in FIG. 9B, the measured amount of change in CBF is significantly smaller than the estimated amount of change in CBF. If such a condition continues, the driving appropriateness determination unit 207 determines that driving appropriateness is not enough. In this case, the driving appropriateness determination unit 207 alerts or warns the driver 402 or switches a driving mode through the display apparatus 206 or the speaker, which is not illustrated. For example, the driving appropriateness determination unit 207 may output a speech sound such as "You look a little tired. Please breathe deeply" to the driver. Alternatively, the driving appropriateness determination unit 207 may automatically increase ventilation, take in outside air, or issue a warning such as "It's dangerous. Please stop the vehicle at a safe place". If the vehicle is provided with a driving assisting system, the driving assisting system may stop the vehicle at a safe place or activate autonomous driving in accordance with the driving appropriateness of the driver.

The system according to the present embodiment is a standalone driver monitoring system that can be additionally mounted on an existing vehicle. All the components illustrated in FIG. 1 are mounted on the integrated system illustrated in FIG. 4A. During these years, vehicles are becoming more intelligent. Vehicles are provide with high-performance arithmetic devices or computers and capable of detecting vehicle conditions by integrating information from various sensors of the vehicles. In addition, vehicles have a communication function such as the Internet and are capable of communicating information with computers outside thereof. In such a vehicle, part of the functions illustrated in FIG. 1 can be incorporated into a computer of the vehicle as software. For example, only the biometric sensing apparatus 106 may be achieved as hardware, and the other functions may be achieved using functions of the vehicle. Some vehicle models can already have a function of authenticating drivers. Vehicle operation information (e.g., acceleration, braking, or steering) detected by a computer of a vehicle can be used as information output from the operation sensing apparatus 102. The computer of the vehicle also includes a storage device. Only the biometric sensing apparatus 106, therefore, may be achieved as unique hardware, and the other functions may be provided for hardware of the vehicle as software. It is thus possible to achieve a certain part of the system illustrated in FIG. 1 as dedicated hardware and another part of the system as software provided for a computer of a vehicle, in accordance with a type of vehicle and vehicle conditions.

A driver's driving appropriateness can be stably monitored constantly while reducing erroneous detection due to individual differences and differences in driving conditions by using the driver monitoring system according to the present embodiment. With this method, the driver can be constantly monitored through noncontact CBF monitoring without causing awkwardness or a sensation of pressure. As a result, safer, more comfortable driving becomes possible.

Second Embodiment

An operation appropriateness determination system according to this embodiment measures an operation stress of an operator. The present embodiment aims to, for example, detect a state of an operation load on an operator who is engaged in office work in which a computer such as a PC is used, improve operation efficiency, and prevent the operator from developing mental health problems. The operation appropriateness determination system evaluates mental loads caused by operations performed at workplaces.

In the first embodiment, an imaging system including a light source that emits temporally modulated pulsed near-infrared light is used to obtain biological information. In the present embodiment, on the other hand, an imaging system including a light source that emits spatially modulated near-infrared light is used to obtain biological information.

During these years, more and more workers are feeling considerable anxiety, worry, or stress about work or working lives. It is therefore desired to actively maintain and improve mental health at workplaces. In a currently conducted "stress check", for example, the following method is used. First, a worker fills in questionnaires about stress. By collecting and analyzing results, a state of the worker's stress can be recognized. Since this method is based on workers' subjective answers, individual differences are large. An indicator of an operation load that serves as a basis of a more objective determination, therefore, is desired. A simple measuring method by which a state of stress can be quantified, for example, is desired.

Various biological signals relating to stress are known. The above-mentioned biological signals such as variation in a heart rate, nose temperature, the frequency of blinking, a respiratory rate, and the depth of respiration are known to be related to a state of stress. A problem caused when these biological signals are used to check stress is individual differences in biological reactions. As illustrated in FIG. 2, individual differences in biological reactions are large, and the biological reactions cannot be used as an objective indicator for evaluating stress as they are. FIG. 2 illustrates a result of fluctuation in a heart rate due to stress. Other physiological indicators known to be correlated with stress cannot be used to directly determine a degree of stress only on the basis of measured values, either. As in the first embodiment, individual differences in biological reactions, reproducibility, and the stability of operation tasks are problems to be addressed.

The operation appropriateness determination system according to the present embodiment is provided as a measure for addressing these problems. As described above, current biological information based on an operation is estimated from a database of operation loads and biological information for each person. Current operation appropriateness is determined by comparing the estimated current biological information and actually measured biological information with each other. With the system according to the present embodiment, changes in an operation load and biological information are constantly learned, and stress caused by a current operation can be constantly estimated in real-time.

The operation appropriateness determination system relating to an operation in which a computer such as a PC is used, too, has the configuration illustrated in FIG. 1A. Operation appropriateness is determined in accordance with the flowchart of FIG. 1B. Since operation appropriateness in an operation in which a computer is used is determined in the present embodiment, a computer such as a PC is used for an operation. The operation appropriateness determination system can be operated using arithmetic performance of the computer used in the operation.

In the present embodiment, only the biometric sensing apparatus 106 is unique hardware among the components illustrated in FIG. 1A. The other components are all stored in the computer as hardware or software. After an operator starts a computer operation, operation appropriateness is determined in the background of the target operation. The biometric sensing apparatus 106, which is hardware different from the computer, is connected to the computer. Information obtained by the biometric sensing apparatus 106 is processed by the computer.

A procedure for determining stress will be described specifically hereinafter with reference to FIG. 1A. In the present embodiment, the authentication apparatus 101 performs personal authentication on the basis of an ID input by an operator. For example, personal authentication is performed when the operator has input an ID and a password using a keyboard connected to the computer such as a PC. In the case of a computer used for business purposes, a person is usually identified from an ID and a password input by the person or through biometric authentication at a stage of login before an operation is started. The system may perform personal authentication using such personal authentication data obtained by the computer.

The operation appropriateness determination system according to the present embodiment may also be referred to as an operation stress measuring system.

Figure 10A:
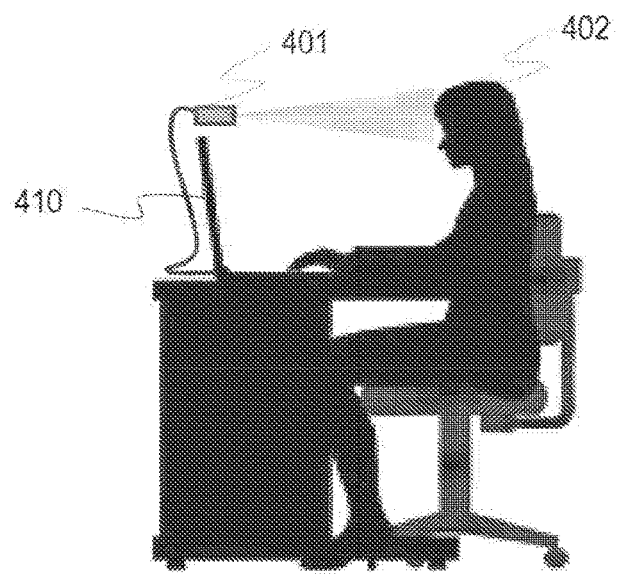
FIG. 10A is a diagram illustrating an example of arrangement of a system for measuring operation stress according to a second embodiment of the present disclosure.

FIG. 10A is a diagram schematically illustrating the overall configuration of the operation appropriateness determination system according to the present embodiment. As with the system according to the first embodiment, the system includes the CBF measuring apparatus 401 as the operation sensing apparatus 102. The CBF measuring apparatus 401 is disposed above a screen of a computer 410 in front of the operator 402. The CBF measuring apparatus 401 according to the present embodiment includes a near-infrared dot array light source and a near-infrared imaging device. The CBF measuring apparatus 401 measures facial blood flow of the operator 402. The system according to the present embodiment is capable of monitoring blood flow under a surface of a face, a heart rate, and variation in the heart rate in a noncontact manner.

Figure 10B:
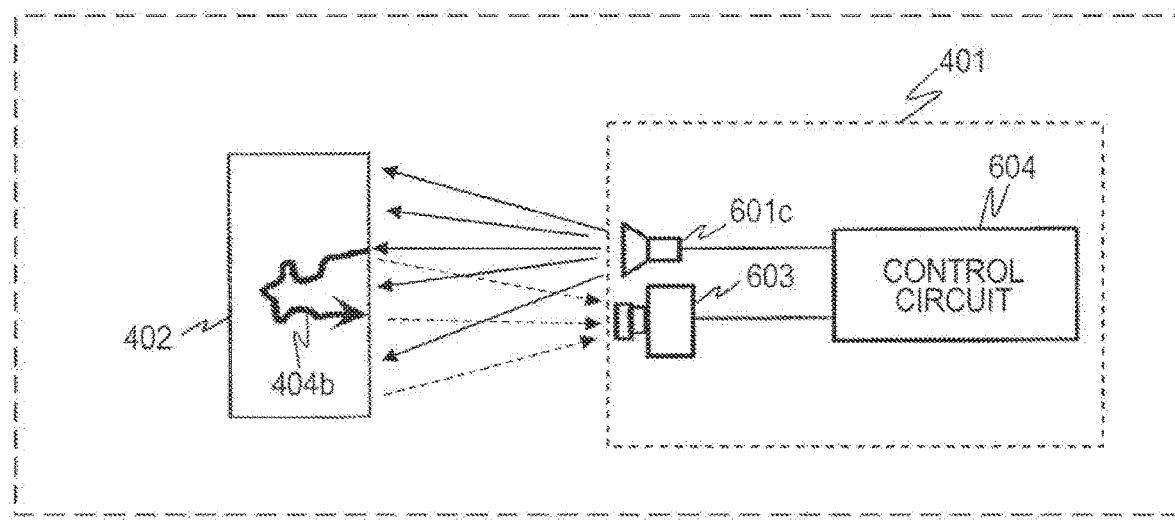
FIG. 10B is a diagram illustrating an example of the configuration of a cerebral blood flow measuring apparatus according to the second embodiment.

FIG. 10B is a diagram illustrating the schematic configuration of the CBF measuring apparatus 401 according to the present embodiment. The CBF measuring apparatus 401 according to the present embodiment includes a light source 601*c*, such as a laser, that projects a dot pattern of near-infrared light, an imaging device 603 that obtains a near-infrared image, and a control circuit 604. The light source 601*c* irradiates a living body (a head of the operator 402 here). The imaging device 603 captures an image of the face of the operator 402 irradiated with near-infrared light. The captured image is analyzed by the control circuit 604. The control circuit 604 may be a processor incorporated into the computer such as a PC, instead. In this case, the CBF measuring apparatus 401 is achieved by a combination of the processor and the light source 601*c* and the imaging device 603 outside the computer.

A signal processing flow for obtaining biological information from an image captured by the imaging device 603 that obtains a near-infrared image will be described with reference to FIGS. 11A to 11O.

Figure 11A:
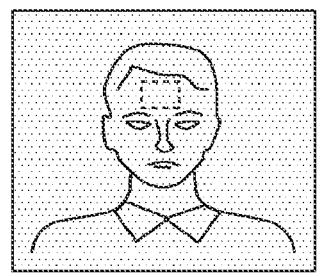
FIG. 11A is a first diagram illustrating signal processing for obtaining biological information according to the second embodiment.

FIG. 11A illustrates an example of a captured near-infrared image. Since the dot array light source is used, bright points corresponding to emission positions of a dot array and relatively weak signals around the bright points are obtained. The relatively weak signals around the bright points are signals corresponding to relatively weak light, which is radiated light that has entered a body, has been scattered inside the body, and has returned to a surface. Human skin has a small absorption coefficient and a large scattering coefficient for near-infrared light. Light that has passed through a skin surface, therefore, goes through repeated multiple scattering inside a body and is output from a wide area of a surface of the body. Alternatively, a light source that projects near-infrared light having a line-space pattern or a checker pattern instead of a dot array pattern, for example, may be used. Similar biological signals can be obtained even when such a light source is used.

Figure 11B:
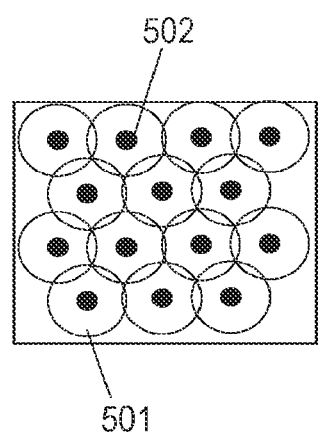
FIG. 11B is a second diagram illustrating the signal processing for obtaining biological information according to the second embodiment.

FIG. 11B is a diagram illustrating an enlarged view of an image of an information detection area of a living body. The information detection area in this example is a forehead area of an operator indicated by a broken line frame in FIG. 11A. Light 501 scattered inside a body returning from below skin is detected around a projected dot pattern of infrared light. Light 502 reflected from a skin surface includes information regarding the skin surface, and the light 501 scattered inside the body includes blood information regarding capillaries inside the body. Blood flow information inside the body can therefore be obtained by performing calculation while extracting, from image data, only data corresponding to the light 501 scattered inside the body.

Figure 11C:
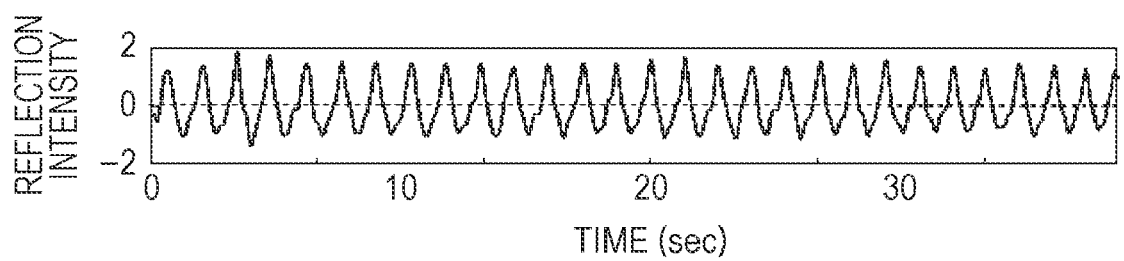
FIG. 11C is a third diagram illustrating the signal processing for obtaining biological information according to the second embodiment.

FIG. 11C illustrates an example of a heart rate signal obtained in this manner. Variation in a heart rate or fluctuation in a heart rate can be obtained from the heart rate signal. Furthermore, since an absolute value of reflection intensity of light scattered inside a body depends on the amount of blood under a surface, the amount of blood can also be calculated from the signal.

With a conventional biological information sensing system employing a camera, a method has been generally used in which pixel data in the entirety of an area corresponding to a living body part of an image is averaged and biological information is detected. The biological information sensing system according to the present embodiment, on the other hand, employs a dot array light source. A component of light reflected from a skin surface, which is unnecessary, can be removed from a two-dimensional image, and light scattered inside a body, which includes biological information, can be selectively extracted. By efficiently extracting light scattered inside a body, biological information can be accurately obtained.

It is known that psychological stress can be estimated from temporal fluctuation in a heart rate. When an autonomic nervous system is functioning normally, intervals between heartbeats fluctuate. It is known, however, that the fluctuation in the intervals between heartbeats becomes less evident due to stress. Presence or absence or a degree of psychological stress can be detected on the basis of changes in the fluctuation in the intervals between heartbeats.

Next, a method for obtaining operation information used by the operation sensing apparatus 102 will be described. In the present embodiment, operation conditions of an operator are detected by analyzing inputs of the computer. In the case of a PC operation, the operator inputs operations to the PC. Operation information can therefore be obtained by monitoring a type of application used and keyboard inputs or mouse inputs. For example, a history of operation information can be easily obtained, such as "the content of an operation is a word processor operation, and the number of characters input in unit time is 50 characters/minute" or "the content of an operation is a spreadsheet software operation, and the number of items input in unit time is 30 items/minute". The operation sensing apparatus 102 according to the present embodiment is achieved by a combination of the processor in the computer and an input device such as a keyboard or a mouse.

Next, the operation of the signal processing apparatus 108 according to the present embodiment will be described.

Figure 12:
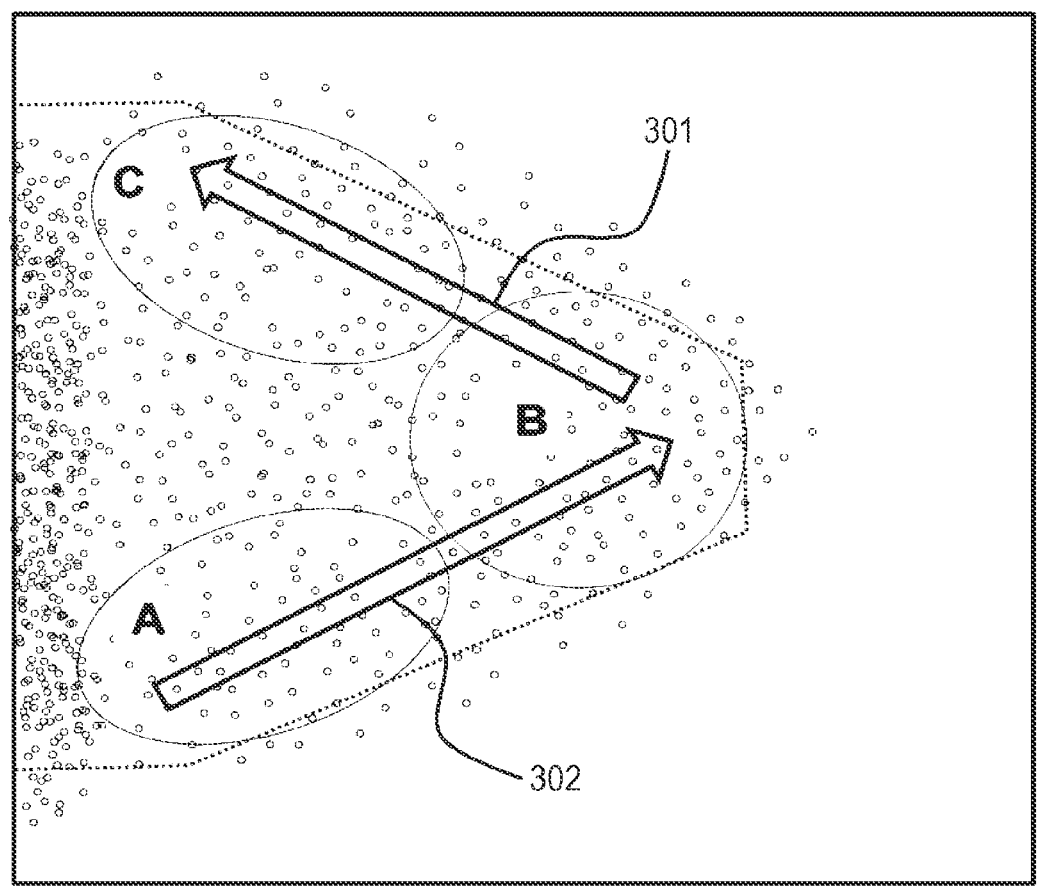
FIG. 12 is a diagram illustrating an example of a relationship between an operation condition and biological information during an operation.

FIG. 12 illustrates data indicating changes in an operation load and biological information regarding an operator in one week obtained by the system according to the present embodiment. The content of an operation was an input operation with a word processor, and the operation load was the number of words input. LF/HF, which is an indicator of the activity of the sympathetic nervous system or an indicator of stress, was used as the biological information. As described above, LF is a low-frequency component of variation in a heart rate, and HF is a high-frequency component. In this example, a range of the high-frequency component was equal to or higher than 0.20 Hz but lower than 0.35 Hz, and a range of the low-frequency component was equal to or higher than 0.05 Hz but lower than 0.20 Hz.

As the number of words input increased and accordingly the operation load increased, LF/HF, which is an indicator of stress, increased as indicated by an arrow 302. When the operator further continued, the operator felt more fatigued. Operation efficiency decreased, and LF/HF as the indicator of stress further increased as indicated by an arrow 301. As described above, however, such a type of reaction greatly varies between individuals, and variation in each person is also great. Stress or a degree of fatigue cannot be simply determined only on the basis of the number of words input and a value of LF/HF.

In the present embodiment, an average distribution obtained by weighting, along a time axis, data for a relatively long period of time illustrated in FIG. 12 is created for each operator from a database of an operation history and biological information regarding the operator. The distribution is used as estimated current biological information. An average distribution for a long period of time represents a relationship between an operation load and biological information unique to each operator. This is because it is considered that if there is no abnormality in an operator, actual biological information will become biological information having a distribution similar to the distribution. On the other hand, data regarding operation loads and biological reactions (e.g., plots in a graph of FIG. 12) obtained as a result of an operation for a relatively short period of time (e.g., about one hour) up to a present time is used as measured current biological information. The above process is performed by the biological information estimation unit 103 of the signal processing apparatus 108. The system according to the present embodiment thus uses operation loads and biological reactions as a frequency map in order to determine operation appropriateness of an operator.

The operation appropriateness determination unit 105 of the signal processing apparatus 108 compares a map of estimated current biological information, that is, an average distribution for a long period of time, and a map of current biological information, that is, an average distribution for a short period of time, with each other. As a result, operation appropriateness of an operator can be determined. If a ratio of data belonging to an area B illustrated in FIG. 12 is higher in a current map than in a map of past data, for example, an operation is being performed with a high level of operation efficiency. If a ratio of data belonging to an area A is high, it is estimated that an operator is not concentrating on an operation, that is, vigilance is low or the operator is tired of the operation. In this case, the operation appropriateness determination system displays, on the display apparatus 107 (e.g., a computer display), an advice such as "You are losing concentration. Please stretch and refresh yourself". If the distribution of current data is mostly concentrated in an area C, it is estimated that operation efficiency has decreased due to fatigue. In this case, the system can display, on the display apparatus 107, some advice such as "You look a little tired. Please take a coffee break". A decrease in operation efficiency can thus be detected and some advice can be given at an appropriate timing by using the system according to the present embodiment. As a result, high operation efficiency can be achieved.

In addition, by using the system, a sign of deteriorated mental health, such as depression, can be detected. As described above, a relationship between operation loads and biological reactions for a relatively long period of time is constantly updated and stored in a database for each operator. By tracing variation in distribution for the long period of time, a sign of depression can be identified. When a depressive tendency gradually appears, the distribution shifts in a direction indicated by the arrow 301 illustrated in FIG. 12. By detecting such a change in the distribution, a depressive tendency can be identified. If such a tendency is observed, for example, an operator can be encouraged to see an industrial physician. It is known that, in the case of depression, the low-frequency component LF of variation in a heart rate, which indicates the activity of the parasympathetic nervous system, decreases. Therefore, not only the relationship between LF/HF and the operation load illustrated in FIG. 12 but also a relationship between LF and the operation load may be monitored. In doing so, a depressive tendency can be detected more accurately.

The system was actually constructed in a computer terminal of an operator who input data using a word processor as operations, and data was obtained for a relatively long period of time. The data was obtained for three months. The operator mainly input data using the word processor as operations.

Figure 13A:
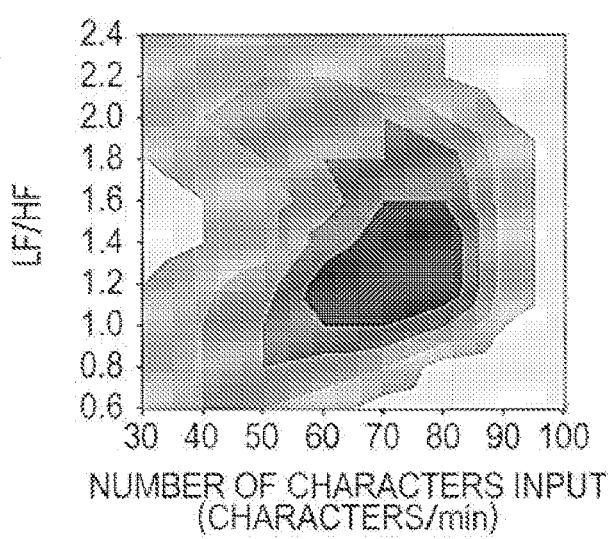
FIG. 13A is a diagram illustrating a distribution of biological information and operation information estimated on the basis of data for a long period of time.
Figure 13B:
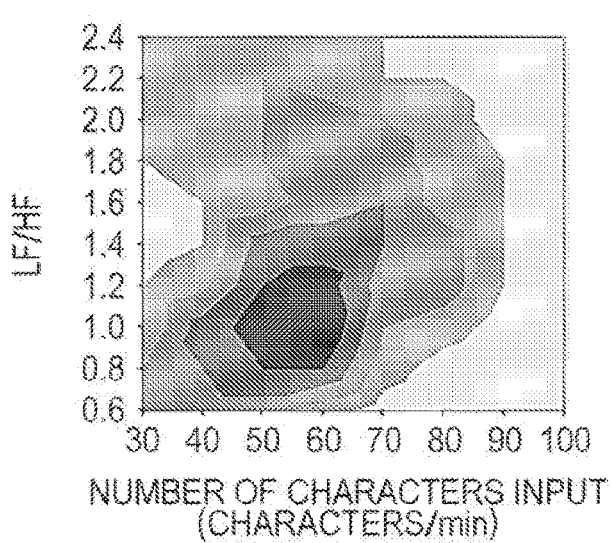
FIG. 13B is a diagram illustrating an example of a distribution of measured biological information.
Figure 13C:
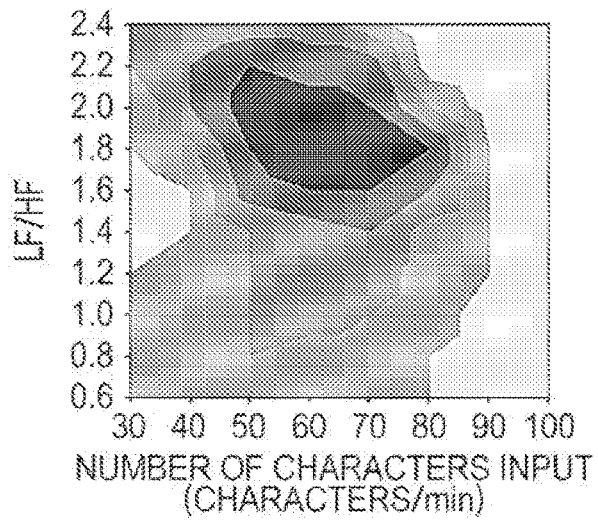
FIG. 13C is a diagram illustrating another example of the distribution of measured biological information.

FIG. 13A illustrates a relationship between the number of characters input in unit time and LF/HF during input operations obtained from the input operations for three months. A darker part indicates a higher frequency. An average input speed was about 75 characters per minute. The value of LF/HF was 1.3 times as high as under normal conditions under which the operator performed no operations. This means that the operator became slightly nervous during the operations. The distribution indicates, for the target operator, a relationship between variation in an operation load and variation in biological information for a long period of time. If there is no abnormality in the operator's physical conditions or mental conditions, the distribution is not significantly deviated from. Such a distribution is used as estimated biological information. Operation appropriateness of the operator was determined by comparing the distribution and current biological information with each other. A distribution of the number of characters input and changes in biological information for a short period of time (every one hour in this example) was obtained as current biological information. During the measurement for three months, two types of characteristic distribution were frequently observed. FIGS. 13B and 13C illustrate an example of the two types of distribution.

In the distribution illustrated in FIG. 13B, the number of characters input is smaller than in the distribution illustrated in FIG. 13A. It can be seen that operation efficiency decreased. In this case, LF/HF, which indicates concentration or stress, was also lower. It can be estimated that the operator was losing concentration at a corresponding time.

In the distribution illustrated in FIG. 13C, on the other hand, the number of characters input is smaller than in the distribution illustrated in FIG. 13A, that is, in this case, too, operation efficiency decreased. LF/HF, which indicates stress, however, was higher than when the operator was performing an operation efficiently. It can be estimated that the operation efficiency of the operator decreased at a corresponding time due to fatigue from the operation.

As described above, although a decrease in operation efficiency can be detected by measuring only the operation efficiency, a cause of the decrease cannot be identified, and an effective measure for improving the operation efficiency cannot be found. By using the system according to the present embodiment, operation appropriateness of an operator can be determined, and an appropriate advice can be given in accordance with a result of the determination. As a result, work productivity can be improved.

As described above, the data indicating the relationship between the operation load and biological information for a long period of time illustrated in FIG. 13A is constantly updated with latest data. By analyzing changes in the distribution, long-term mental health conditions of an operator can be checked. If a high-frequency part illustrated in FIG. 13A gradually moves in a direction indicated by the arrow 301 illustrated in FIG. 12, for example, it can be seen that some mental health problem can be arising. It is important especially in terms of work safety to identify mental health problems at early stages and take appropriate measures.

As described above, by comparing a distribution of an operation load and biological information for a relatively long period of time and a current distribution of an operation load and biological information for a relatively short period of time with each other, current operation efficiency and operation appropriateness can be determined. In addition, by monitoring temporal changes in the distribution of an operation load and biological information for a relatively long period of time, measures can be efficiently taken for mental health problems.

Third Embodiment

This embodiment is about an operation appropriateness determination system that aims to improve the efficiency of learning in which a computer such as a PC is used. The operation appropriateness determination system according to the present embodiment can also be referred to as a "learning appropriateness determination system". The system can be used, for example, in a school, a cram school, or online learning. An operator in the present embodiment is a learner, and the content of an operation is learning in which a computer is used.

During these years, a market for various learning systems and learning materials employing computers is expanding. Such a system is advantageous in that a learner can learn at any time he/she likes. There is a problem, however, in that because no teacher is present, the learner tends to lose concentration and it becomes hard to produce desirable results. In order to solve this problem, the present embodiment provides a system that determines concentration or learning appropriateness of a learner and that gives feedback to the learning during the learning. In the present embodiment, as in the second embodiment, a computer is used. Therefore, in the present embodiment, too, the same hardware configuration as that according to the second embodiment can be used. As illustrated in FIG. 10A, the CBF measuring apparatus 401 is an only piece of unique hardware and connected to the computer 410 such as a PC. The components illustrated in FIG. 1A other than the CBF measuring apparatus 401 are all stored in the computer 410 as hardware or software. After an operator starts a computer operation, the computer 410 determines operation appropriateness in the background of the target operation. Learning software operates in combination with the system, and content of learning can change in accordance with a learner's understanding and concentration, which achieves efficient learning.

In the present embodiment, too, personal authentication is performed by inputting an ID using the computer such as a PC.

The hardware configuration of the CBF measuring apparatus 401 is the same as that according to the second embodiment. As illustrated in FIG. 10B, the CBF measuring apparatus 401 includes the light source 601c, which is a near-infrared dot array light source, and the imaging device 603. The system according to the second embodiment measures a heart rate from changes in facial blood flow and uses fluctuation in the heart rate as biological information. The system according to the present embodiment, on the other hand, determines concentration from changes in nasal blood flow.

A signal processing flow for obtaining biological information from an image captured by the imaging device 603 will be described with reference to FIGS. 14A to 14C.

Figure 14A:
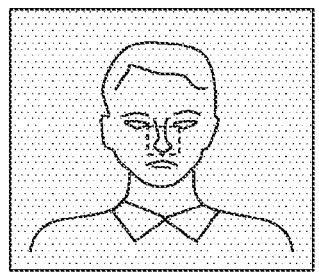
FIG. 14A is a first diagram illustrating signal processing for obtaining biological information according to a third embodiment.
Figure 14B:
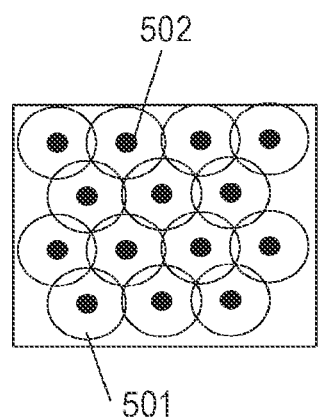
FIG. 14B is a second diagram illustrating the signal processing for obtaining biological information according to the third embodiment.
Figure 14C:
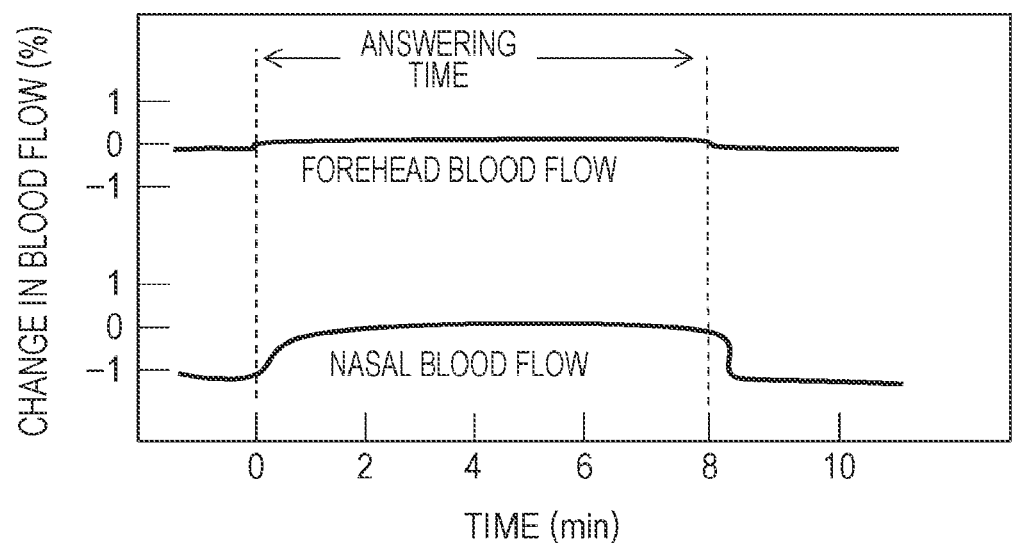
FIG. 14C is a third diagram illustrating the signal processing for obtaining biological information according to the third embodiment.

FIG. 14A illustrates an example of a captured near-infrared image. FIG. 14B is a diagram illustrating an enlarged view of an image of an information detection area of a living body. In this example, the information detection area of the living body is a nose area indicated by a broken line frame in FIG. 14A. Light 501 scattered under skin is detected around a projected dot pattern. Blood flow information inside the body can be obtained by performing calculation while extracting, from image data, only data corresponding to the light 501 scattered inside the body. FIG. 14C illustrates an example of the blood flow information obtained in this manner. When blood flow increases, reflectance decreases due to absorption of light by blood. Changes in the blood flow can therefore be detected from a signal of reflected light. A difference between the signal illustrated in FIG. 14C and the signal illustrated in FIG. 11C is the width of a vertical axis, that is, changes in reflectance due to variation in a heart rate are smaller than changes in blood flow. FIG. 14C illustrates results obtained after an effect of variation in a heart rate is removed by performing time moving averaging. FIG. 14C illustrates not only a result of measurement performed in a nose but also a result of measurement of changes in blood flow in a forehead, which is data for comparison.

It is known that nose temperature changes due to stress. Anastomoses between arteries and veins called "arteriovenous anastomotic vessels" under the control of the sympathetic nervous system are concentrated in and around the nose. Changes in blood flow caused by activation or inactivation of an autonomous nervous system directly influence changes in skin temperature of the nose. When a person is nervous or stressed, the autonomous nervous system is activated, and blood flow decreases. As a result, the skin temperature of the nose decreases. Psychological stress or concentration has been conventionally evaluated by monitoring the skin temperature of and around the nose through thermography. In the system according to the present embodiment, the near-infrared imaging device directly evaluates changes in blood flow that cause changes in temperature instead of measuring the temperature. As described above, more arteriovenous anastomotic vessels are concentrated in the nose than in other body parts, and the blood flow in the nose is greatly affected by changes in the autonomous nervous system. The blood flow in the forehead, on the other hand, is stable and hardly affected by changes in the autonomous nervous system and closely related to temperature of a deep part of the body. The system according to the present embodiment therefore measures both changes in the blood flow in the forehead and changes in the blood flow in the nose and uses a result of the measurement of the forehead as a reference. As a result, an effect of disturbances such as changes in the illuminance of radiated light and bodily motions can be removed, and presence or absence or a degree of psychological stress can be stably detected on the basis of changes in the blood flow in the nose.

Next, a method for obtaining operation information used by the operation sensing apparatus 102 according to the present embodiment will be described. A learner learns in accordance with instructions from software (hereinafter referred to as "learning software") installed on, for example, a PC, a tablet computer, or the like. The computer therefore constantly identifies content of the learning. The CBF measuring apparatus 401 according to the present embodiment measures changes in blood flow at a time when the learning software presents a problem and the learner answers the problem. The CBF measuring apparatus 401 obtains data such as that illustrated in FIG. 14C. When the learner concentrates on solving the problem, the blood flow in the nose decreases, and reflectance of near-infrared light increases.

Next, the operation of the biological information estimation unit 103 of the signal processing apparatus 108 will be described. In the present embodiment, too, the biological information estimation unit 103 analyzes data regarding operation loads of learners and biological reactions for long periods of time and constructs a database for each person in the storage device 104. An operation load in the present embodiment is a problem solving condition, and biological reactions are changes in the blood flow in the nose. Data regarding time taken until a learner solves each problem after the problem is presented, the difficulty of problems, and whether the learner has correctly solved each problem can be obtained from the computer 410. The biological information estimation unit 103 calculates an average change in the learner's blood flow in the nose under such conditions on the basis of the data. In the present embodiment, the average change is used as an estimated value of biological information.

The operation appropriateness determination unit 105 of the signal processing apparatus 108 compares an estimated current amount of change in the blood flow in the nose and an actually measured amount of change in the blood flow in the nose with each other. As a result, learning conditions of the learner can be detected. If the learner has solved a problem earlier than estimated and the amount of change in the blood flow in the nose is smaller than an estimated value, it can be determined that the problem is too easy for a current learning level of the learner. In this case, it can be determined that a more difficult problem is to be presented or that the learner is to advance to a next learning step. If the learner has solved a problem later than estimated and the amount of change in the blood flow in the nose is smaller than the estimated value, the learner is losing concentration on the learning. An alert can be issued or an advice to refresh himself/herself can be provided on a display of the computer. If the learner has not solved a problem even though the amount of change in the blood flow in the nose is large and the learner has concentrated on the problem, it is estimated that the learner's understanding of a range of learning is insufficient. In this case, a problem for identifying a lack of understanding of the learner can be presented or content of learning can be changed such that the learner can learn an important part again. If the amount of change in the blood flow in the nose is large, and the learner has concentrated on solving a problem and solved the problem, it is estimated that learning is going well. In this case, it can be determined that a more difficult problem is to be presented or that the learner is to advance to a more difficult content of learning. The operation appropriateness determination unit 105 thus provides a learner with learning content according to operation appropriateness in accordance with a result of a determination made for the learner.

As described above, understanding of learning or concentration can be determined as operation appropriateness by using the system according to the present embodiment. A computer can provide learning content or an alert according to a result of the determination of the operation appropriateness of a learner. As a result, the learner can efficiently learn while maintaining concentration.

The present disclosure also includes a computer program that specifies an operation to be performed by the signal processing apparatus 108 illustrated in FIG. 1A. The computer program is stored in a storage medium such as a memory in the operation appropriateness determination system and causes the signal processing apparatus 108 to perform the above-described operations.

What is claimed is:

1. A method comprising:
obtaining biological information regarding an operator who is performing an operation, the operation including at least a keyboard input or a mouse operation;
obtaining operation information which relates to the operation;
accumulating, while the operator is performing the operation, the biological information and the operation information in a storage device while associating the biological information and the operation information with one another;
determining parameters for calculating the biological information at a present time by performing machine learning based on (i) a correlation between the biological information during a past time period and the operation information during the past time period, the correlation being accumulated in the storage device;
calculating the biological information at the present time based on the parameters and (iii) the operation information at the present time;
determining appropriateness of the operator for the operation at the present time based on (ii) the biological information obtained at the present time and the biological information at the present time calculated based on the operation information at the present time; and
upon determining that a variation between the biological information obtained at the present time and the biological information at the present time calculated based on the operation information at the present time is greater than a variation calculated from past data, automatically increasing ventilation of a workplace, automatically taking in outside air into the workplace, or automatically increasing ventilation of the workplace and automatically taking in outside air into the workplace, by a signal processing apparatus.

2. The method according to claim 1, wherein the operation includes the keyboard input.

3. The method according to claim 2, further comprising:
obtaining, from the keyboard input or authentication apparatus, identifying information for identifying the operator; and accumulating the identifying information while associating the biological information, the operation information, and the identifying information with one another.

4. The method according to claim 1, wherein the operation information includes information which relates to the number of words input by the keyboard.

5. The method according to claim 1, further comprising: outputting an image or a sound indicating advice about the operation in accordance with the appropriateness of the operator.

6. The method according to claim 1, wherein the appropriateness of the operator refers to a degree of at least one mental state selected from a group consisting of concentration, fatigue, and stress.

7. A system comprising:
a biometric sensing apparatus that obtains biological information regarding an operator who is performing an operation, the operation including at least a keyboard input or a mouse operation;
an operation sensing apparatus that obtains operation information which relates to the operation;
a storage device; and
a signal processing apparatus, wherein:
the signal processing apparatus
accumulates, while the operator is performing the operation, the biological information and the operation information in the storage device while associating the biological information and the operation information with one another,
determines parameters for calculating the biological information at a present time by performing machine learning based on (i) a correlation between the biological information during a past time period and the operation information during the past time period, the correlation being accumulated in the storage device,
calculates the biological information at the present time based on the parameters and (iii) the operation information at the present time,
determines appropriateness of the operator for the operation at the present time based on (ii) the biological information obtained at the present time and the biological information at the present time calculated based on the operation information at the present time, and
upon determining that a variation between the biological information obtained at the present time and the biological information at the present time calculated based on the operation information at the present time is greater than a variation calculated from past data, automatically increases ventilation of a workplace, automatically takes in outside air into the workplace, or automatically increases ventilation of the workplace and automatically takes in outside air into the workplace, by the signal processing apparatus.

8. The method according to claim 1, wherein obtaining the biological information includes:
detecting a heartbeat signal of the operator by using a non-contact biological sensing device; and
calculating a high-frequency component and a low-frequency component of heartbeat rate fluctuation from the heartbeat signal, as the biological information.

* * * * *